US008569562B2

(12) United States Patent
Feher et al.

(10) Patent No.: US 8,569,562 B2
(45) Date of Patent: Oct. 29, 2013

(54) PURIFICATION OF ISOPRENE FROM RENEWABLE RESOURCES

(75) Inventors: Frank J. Feher, Copley, OH (US); John Kaluen Kan, San Mateo, CA (US); Joseph C. McAuliffe, Sunnyvale, CA (US); Thomas F. McCall, Overland Park, KS (US); Stephan Rodewald, Canal Fulton, OH (US); Timothy Alan Sabo, Southington, OH (US); Tang Hong Wong, Hudson, OH (US); Christopher D. Ploetz, Fairway, KS (US); Lawrence J. Pickert, Overland Park, KS (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 156 days.

(21) Appl. No.: 12/969,440

(22) Filed: Dec. 15, 2010

(65) Prior Publication Data

US 2011/0178261 A1 Jul. 21, 2011

Related U.S. Application Data

(60) Provisional application No. 61/288,142, filed on Dec. 18, 2009.

(51) Int. Cl.
*C07C 7/00* (2006.01)
(52) U.S. Cl.
USPC .......................................... 585/810; 585/800
(58) Field of Classification Search
USPC ....................................................... 585/810
See application file for complete search history.

(56) References Cited

U.S. PATENT DOCUMENTS

| | | | |
|---|---|---|---|
| 3,146,278 A | 8/1964 | Habeshaw et al. | |
| 3,437,711 A | 4/1969 | Yanagita et al. | |
| 3,510,405 A * | 5/1970 | Takeo et al. ...................... | 203/9 |
| 3,574,780 A | 4/1971 | Watanabe et al. | |
| 3,621,072 A | 11/1971 | Watanabe et al. | |
| 3,662,016 A | 5/1972 | Furuoya et al. | |

(Continued)

FOREIGN PATENT DOCUMENTS

| | | |
|---|---|---|
| EP | 2 145 665 A2 | 1/2010 |
| GB | 819188 A | 9/1959 |

(Continued)

OTHER PUBLICATIONS

Bunge, M. et al. (Apr. 2008). "On-Line Monitoring of Microbial Volatile Metabolites by Proton Transfer Reaction-Mass Spectrometry," *Applied and Environmental Microbiology* 74(7):2179-2186.

(Continued)

*Primary Examiner* — In Suk Bullock
*Assistant Examiner* — Philip Louie
(74) *Attorney, Agent, or Firm* — Morrison & Foerster LLP

(57) ABSTRACT

Methods and apparatus for the purification of isoprene, such as the purification of a bioisoprene composition from fermentor off-gas. The apparatus includes two columns that process the fermentor off-gas, which includes isoprene and various impurities. A solvent is added to the off-gas in the first column, and the isoprene is stripped from the solvent in the second column. Also provided is a downstream further purification process. Also provided are the resulting purified isoprene compositions.

33 Claims, 9 Drawing Sheets

(56) References Cited

U.S. PATENT DOCUMENTS

| | | | |
|---|---|---|---|
| 3,972,955 | A | 8/1976 | Halcour et al. |
| 4,000,209 | A | 12/1976 | Downs et al. |
| 4,014,952 | A | 3/1977 | Adema et al. |
| 4,067,923 | A | 1/1978 | Belyaev et al. |
| 4,147,848 | A | 4/1979 | Arakawa et al. |
| 4,511,751 | A | 4/1985 | Ninagawa et al. |
| 4,570,029 | A | 2/1986 | Kulprathipanja et al. |
| 4,703,007 | A | 10/1987 | Mulholland et al. |
| 5,035,794 | A | 7/1991 | Atwood |
| 5,849,970 | A | 12/1998 | Fall et al. |
| 6,500,970 | B1 * | 12/2002 | Barnicki et al. ............ 549/538 |
| 6,987,152 | B1 | 1/2006 | Eisinger et al. |
| 7,442,233 | B2 | 10/2008 | Mitariten |
| 8,288,148 | B2 * | 10/2012 | Cervin et al. ............ 435/252.33 |
| 8,450,549 | B2 * | 5/2013 | McAuliffe et al. ........... 585/508 |
| 2008/0038805 | A1 | 2/2008 | Melis |
| 2010/0048964 | A1 | 2/2010 | Calabria et al. |
| 2010/0086978 | A1 | 4/2010 | Beck et al. |
| 2010/0113846 | A1 * | 5/2010 | McAuliffe et al. ............ 585/16 |
| 2010/0167370 | A1 | 7/2010 | Chotani et al. |
| 2010/0167371 | A1 | 7/2010 | Chotani et al. |
| 2010/0184178 | A1 | 7/2010 | Beck et al. |
| 2010/0196977 | A1 | 8/2010 | Chotani et al. |
| 2010/0216958 | A1 * | 8/2010 | Peters et al. ................. 526/258 |
| 2010/0261942 | A1 * | 10/2010 | McPhee ...................... 585/603 |
| 2011/0014672 | A1 | 1/2011 | Chotani et al. |
| 2011/0040058 | A1 * | 2/2011 | McAuliffe et al. ........... 526/337 |
| 2011/0046422 | A1 | 2/2011 | McAuliffe et al. |

FOREIGN PATENT DOCUMENTS

| | | | |
|---|---|---|---|
| WO | WO-2004/033646 | A2 | 4/2004 |
| WO | WO-2004/033646 | A3 | 4/2004 |
| WO | WO-2009/076676 | A2 | 6/2009 |
| WO | WO-2009/076676 | A3 | 6/2009 |
| WO | WO-2010/001078 | A2 | 1/2010 |
| WO | WO-2010/001078 | A3 | 1/2010 |
| WO | WO-2010/001078 | A4 | 1/2010 |
| WO | WO-2010/101855 | A2 | 9/2010 |
| WO | WO-2010/101855 | A3 | 9/2010 |
| WO | WO-2011/075534 | A2 | 6/2011 |
| WO | WO-2011/075534 | A3 | 6/2011 |

OTHER PUBLICATIONS

Crueger, W. et al. (1989). *Biotechnology: A Textbook of Industrial Microbiology*, Second Edition, Brock, T.D. ed., Sinauer Associates, Inc.: Sunderland, MA, pp. vii-x, (Table of Contents Only).

Dang, H. (2001). "$CO_2$ Absorption Rate and Solubility in Monoethanolamine/Peperazine/Water," *Prepared for presentation at the First National Conference on Carbon Sequestration*, Washington, DC, May 14-17, 2001, 17 pages.

Gerhardt, P. et al. eds. (1994). *Methods for General and Molecular Bacteriology*, American Society for Microbiology: Washington, D.C., p. v, (Table of Contents Only).

Hale, W.G. et al. (1991). *The Harper Collins Dictionary of Biology*, Ehrlich, E. ed., Harper Perennial: New York, NY, 2 pages.

Rimbault, A. et al. (1986). "Headspace Gas Chromatographic-Mass Spectrometric Analysis of Light Hydrocarbons and Volatile Organosulphur Compounds in Reduced-Pressure Cultures of *Clostridium*," *Journal of Chromatography* 375:11-25.

U.S. Appl. No. 61/187,930, filed Jun. 17, 2009, by Wells et al.
U.S. Appl. No. 61/187,934, filed Jun. 17, 2009, by Chotani et al.
U.S. Appl. No. 61/187,959, filed Jun. 17, 2009, by McAuliffe et al.
U.S. Appl. No. 61/187,944, filed Jun. 17, 2009, by McAuliffe et al.
International Search Report mailed on Feb. 22, 2012, for PCT Patent Application No. PCT/US2010/060552, filed on Dec. 15, 2010, published on Apr. 12, 2012, as WO 2011/075534, 4 pages.

* cited by examiner

PURIFICATION OF ISOPRENE FROM RENEWABLE RESOURCES

CROSS REFERENCE TO RELATED APPLICATION

This application claims priority to U.S. Provisional Application No. 61/288,142, filed Dec. 18, 2009, incorporated herein by reference in its entirety.

FIELD OF THE INVENTION

This disclosure relates to production of isoprene.

BACKGROUND

Isoprene (2-methyl-1,3-butadiene) is an important organic compound used in a wide array of applications. For instance, isoprene is employed as an intermediate or a starting material in the synthesis of numerous chemical compositions and polymers. Isoprene is also an important biological material that is synthesized naturally by many plants and animals, including humans.

Isoprene became an important monomer for utilization in the synthesis of cis-1,4-polyisoprene when its stereo-regulated polymerization became commercially possible in the early 1960s. cis-1,4-Polyisoprene made by such stereo-regulated polymerizations is similar in structure and properties to natural rubber. Even though it is not identical to natural rubber, it can be used as a substitute for natural rubber in many applications. For instance, synthetic cis-1,4-polyisoprene rubber is widely used in manufacturing vehicle tires and other rubber products. This demand for synthetic cis-1,4-polyisoprene rubber consumes a majority of the isoprene available in the worldwide market. The remaining isoprene is used in making other synthetic rubbers, block copolymers, and other chemical products. For instance, isoprene is used in making butadiene-isoprene rubbers, styrene-isoprene copolymer rubbers, styrene-isoprene-butadiene rubbers, styrene-isoprene-styrene block copolymers, and styrene-isoprene block copolymers.

Over the years, many synthesis routes for producing isoprene have been investigated. For instance, the synthesis of isoprene by reacting isobutylene with formaldehyde in the presence of a catalyst is described in U.S. Pat. Nos. 3,146,278, 3,437,711, 3,621,072, 3,662,016, 3,972,955, 4,000,209, 4,014,952, 4,067,923, and 4,511,751. U.S. Pat. No. 3,574,780 discloses another process for the manufacture of isoprene by passing a mixture of methyl-tert-butyl ether and air over mixed oxide catalysts. The methyl-tert-butyl ether is then cracked into isobutylene and methanol over the catalyst. The methanol produced is oxidized into formaldehyde which then reacts with the isobutylene over the same catalyst to produce the isoprene. U.S. Pat. No. 5,177,290 discloses a process for producing dienes, including isoprene, which involves reacting a reaction mixture of a tertiary alkyl ether and a source of oxygen over two functionally distinct catalysts under reaction conditions sufficient to produce high yields of the dienes with minimal recycle of the tertiary alkyl ether and tertiary alkyl ether decomposition products.

The isoprene used in industrial applications is typically produced as a by-product of the thermal cracking of petroleum or naphtha or is otherwise extracted from petrochemical streams. This is a relatively expensive energy-intensive process. With the worldwide demand for petrochemical based products constantly increasing, the cost of isoprene is expected to rise to much higher levels in the long-term and its availability is limited in any case. There is concern that future supplies of isoprene from petrochemical-based sources will be inadequate to meet projected needs and that prices will rise to unprecedented levels. Accordingly, there is a need to procure a source of isoprene from a low cost, renewable source which is environmentally friendly.

Several recent advancements have been made in the production of isoprene from renewable sources (see, for example, International Patent Application Publication No. WO2009/076676). These production techniques often results in isoprene compositions containing various amounts of impurities as part of the fermentation process. For example, fermentation may generate volatile components, such as water vapor from the fermentation media, carbon dioxide as a respiration product, and residual oxygen in case of aerobic metabolism, as well as other organic bio-byproducts. Oxygen may initiate unwanted chemical reactions of isoprene, reducing yield and generating undesirable reaction products. Carbon dioxide is a known inhibitor for subsequent catalytic reactions for conversion and application of isoprene, such as isoprene to polymers, such as dimers, trimers, up to very long-chained polymers such as synthetic rubber. Water vapor and other residual bio-byproducts are also undesirable for many applications using isoprene. Accordingly, purification techniques and methods for isoprene compositions produced from renewable resources are desirable.

The disclosures of all publications, patents, patent applications and published patent applications referred to herein are hereby incorporated herein by reference in their entirety.

SUMMARY

The present disclosure provides, inter alia, methods and apparatus for purifying isoprene from renewable resources or similar and the resulting purified isoprene compositions.

In one aspect there is provided a method of purifying isoprene from a fermentor off-gas, wherein the off-gas comprises isoprene, volatile impurity, and bio-byproduct impurity, the method comprising: contacting the fermentor off-gas with a solvent in an apparatus including a first column to form: an isoprene-rich solution comprising the solvent, a major portion of the isoprene and a major portion of the bio-byproduct impurity; and a vapor comprising a major portion of the volatile impurity; transferring the isoprene-rich solution from the first column to a second column; and stripping isoprene from the isoprene-rich solution in the second column to form: an isoprene-lean solution comprising a major portion of the bio-byproduct impurity; and a purified isopene composition. In some embodiments, the off-gas is a bioisoprene composition.

In any of these embodiments, the volatile impurity comprises a compound selected from $H_2O$, $CO_2$, $N_2$, $H_2$, $CO$ and $O_2$. In some embodiments, the volatile impurity comprises $H_2O$, $CO_2$, and $N_2$. In some embodiments, the volatile impurity comprises about 25 to about 80 mol % $CO_2$, about 45 to about 99 mol % $N_2$, and optionally comprises less than about 50 mol % $O_2$. In some embodiments, the volatile impurity comprises about 40 to about 60 mol % $CO_2$, about 65 to about 99 mol % $N_2$, and optionally comprises less than about 25 mol % $O_2$.

In any of these embodiments, the bio-byproduct impurity comprises a polar or non- or semi-polar impurity. In some embodiments, the bio-byproduct impurity comprises one, two, three, or more compounds selected from ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatetraene and (E)-7,11-dimethyl-3-methylene-1,6,10-dodecatriene, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3-methyl-1,3-pentadiene, (Z)-3-methyl-1,3-pentadiene. In some embodiments, in the fermented off-gas the amount of bio-byproduct relative to amount of isoprene is greater than about 0.01% (w/w), or greater than about 0.05% (w/w).

In any of these embodiments, the solvent is a non-polar high-boiling point solvent. In some embodiments, the solvent has a boiling point of greater than about 350° F., or greater than about 375° F. In some embodiments, the solvent has a $CO_2$ Ostwald coefficient at 130° F. of less than about 1.25, or less than about 1.1. In some embodiments, the solvent has a Kauri-butanol value of less than about 50, or from about 20 to about 30, or from about 23 to about 27. In some embodiments, the solvent has an Aniline Point of greater than about 150° F., or from about 175° F. to about 200° F. In some embodiments, the solvent has a kinematic viscosity at 40° C. is less than about 2.5 centistokes (cSt), or less than about 1.75 centistokes (cSt). In some embodiments, the solvent has a surface tension at 25° C. from about 20 to 30 dyne/cm, or about 23 to 27 dyne/cm. In some embodiments, the solvent has an average molecular weight from about 125 to about 225 u, or from about 140 to about 200 u (hereinafter without the "u"). In some embodiments, the solvent is a selected from a terpene, a paraffin, a monoaromatic hydrocarbon, a polyaromatic hydrocarbon, or a mixture thereof. In some embodiments, the solvent is a paraffin (e.g., a C10-C20 paraffin, such as a C12-C14 paraffin). In some embodiments, the solvent is selected from a solvent substantially similar to Isopar™ L, Isopar™ H and Isopar™ M. In some embodiments, the solvent is selected from Isopar™ L, Isopar™ H and Isopar™ M. In some embodiments, the solvent is substantially similar to Isopar™ L. In some embodiments, the solvent is Isopar' L. In some embodiments, the solvent further comprises a polymerization inhibitor. In some embodiments, the polymerization inhibitor is selected from 2,2,6,6-Tetramethylpiperidine 1-oxyl (TEMPO); 4-Hydroxy-2,2,6,6-tetramethylpiperidine 1-oxyl (TEMPOL); Bis(1-oxyl-2,2,6,6-tetramethylpiperidine-4-yl)sebacate (bridged TEMPO); and t-butyl catechol. In some embodiments, the concentration of the polymerization inhibitor is from about 0.001% to about 0.1% (w/w) relative to the concentration of isoprene.

In any of these embodiments, the temperature of the fermentor off-gas is reduced prior to contacting the solvent in the first column.

In any of these embodiments, the fermentor off-gas is transferred to an isolation unit capable of stabilizing the off-gas pressure prior to contacting the fermentor off-gas with the solvent in the first column.

In any of these embodiments, the fermentor off-gas is at least partially condensed prior to contacting the solvent in the first column.

In any of these embodiments, the step of contacting the fermentor off-gas with a solvent in a first column comprises cooling the feed solvent. The lean solvent stream is cooled or chilled before being fed to the first column, e.g., to 4° C. (40° F.).

In some embodiments, the bottom stream from the first (or second) column is reboiled to greater than about 66° C. (150° F.), or greater than about 91° C. (200° F.). In some embodiments, that bottom stream is reboiled from about 93° C. (200° F.) to about 135° C. (275° F.), or from about 110° C. (230° F.) to about 121° C. (250° F.). The reboiling strips $CO_2$, which is a volatile impurity, from the isoprene rich solvent.

In any of these embodiments, the step of contacting the fermentor off-gas with a solvent in a first column further comprises adding steam to the first column as an alternative to reboiling the bottom stream, which is necessary under certain operating conditions.

In any of these embodiments, the step of stripping isoprene from the isoprene-rich solution in the second column comprises adding steam to the second column as an alternative to the reboiling.

In any of these embodiments, the method further comprises transferring the purified isoprene-lean solution to the first column for reuse. In some embodiments, the method further comprises: purifying the isoprene-lean solution to remove a major portion of the bio-byproduct impurity; and transferring the purified isoprene-lean solution to the first column for reuse. In some embodiments, purifying the isoprene-lean solution comprises treating the isoprene-lean solution with an adsorption system. In some embodiments, the adsorption system comprises activated carbon, alumina, silica, or Selexsorb® (from BASF). In some embodiments, the adsorption system comprises silica. In some embodiments, purifying the isoprene-lean solution comprises distillation. In some embodiments, purifying the isoprene-lean solution comprises liquid-liquid extraction.

In any of these embodiments, the temperature of the isoprene-lean solution is reduced prior to removing a major portion of the bio-byproduct impurity. In some embodiments, the temperature of the isoprene-lean solution is reduced to less than about 66° C. (150° F.), or to less than about 38° C. (100° F.), or to less than about 24° C. (75° F.).

In any of these embodiments, the method comprises further purifying the purified isoprene composition. In some embodiments, purifying the isoprene comprises distillation (e.g., after the purified isoprene composition is transferred from the second column to a reflux condenser). In some embodiments, further purifying the purified isoprene composition comprises treating the purified isoprene composition with an adsorption system. In some embodiments, the adsorption system comprises activated carbon, alumina, silica, or Selexsorb®. In some embodiments, the adsorption system comprises silica.

In any of these embodiments, the method further comprises removing from vapor a minor portion of the isoprene, if present. In some embodiments, removing a minor portion of the isoprene, if present, comprises treating vapor with an adsorption system. In some embodiments, the adsorption system comprises activated carbon, alumina, silica, or Selexsorb®. In some embodiments, the adsorption system comprises activated carbon.

In any of these embodiments, the fermentor off-gas is provided to the first column at greater than atmospheric pressure.

In any of these embodiments, the purified isoprene composition has a purity of greater than about 90%, or greater than about 95%, or greater than about 99%.

In any of these embodiments, the purified isoprene composition comprises less than about 25% bio-byproduct impurity relative to the bio-byproduct impurity of the fermentor off-gas, or less than about 10%, or less than about 5%.

In any of these embodiments, the purified isoprene composition comprises less than about 2.5% water and 0.25% $CO_2$, $O_2$, and $N_2$ as volatile impurities relative to the volatile impurity of the fermentor off-gas, or less than about 0.10%, or less than about 0.05% of these impurities.

In another aspect is provided a purified isoprene composition preparable by any one of the methods described herein. In some embodiments there is provided purified isoprene composition prepared by any one of the methods described herein.

In another aspect there is provided an isoprene composition. In some embodiments, the composition comprises isoprene, and bio-byproduct impurity, wherein the bio-byproduct impurity comprises C5 hydrocarbons, and there is greater than about 99.94% isoprene (w/w) relative to the weight of C5 hydrocarbons, and less than about 0.05% bio-byproduct (w/w) relative to the weight of the isoprene. In some embodiments, the bio-byproduct comprises one or more compounds as listed above, and including those selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-but-1-enyl acetate, 3-methyl-2-but-1-enyl acetate, (E)-3,7-dimethyl-1,3,6-octatriene, (Z)-3,7-dimethyl-1,3,6-octatriene, and 2,3-cycloheptenolpyridine. In some embodiments, the composition comprises less than about 5% volatile impurity relative to the weight of the composition. In some embodiments, the composition comprises isoprene at greater than about 95% relative to the weight of the composition.

DETAILED DESCRIPTION

Figure 1:
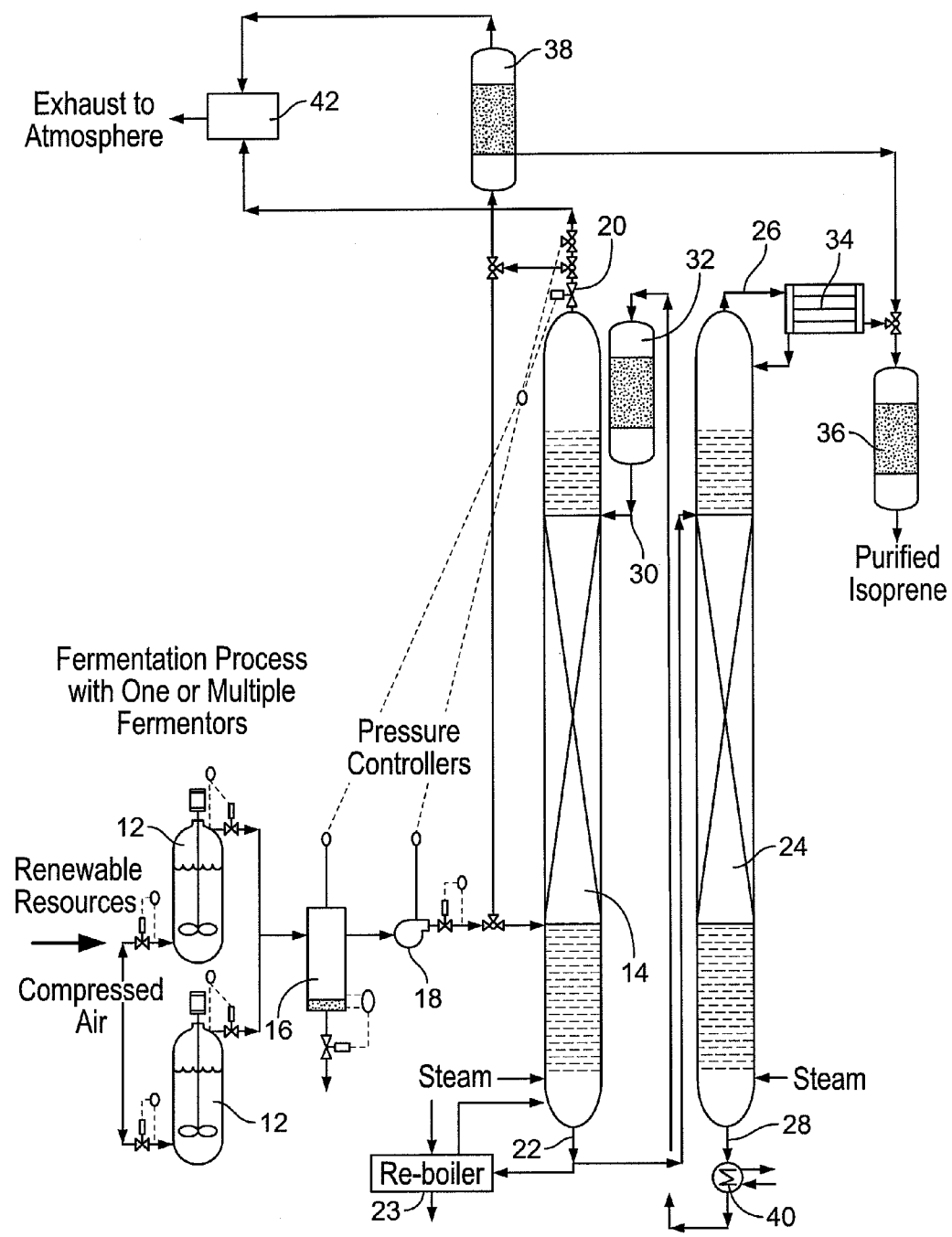
FIG. 1 is a diagram of a process and associated apparatus for purifying isoprene as described herein.

This disclosure provides, inter alia, methods and apparatus for purifying isoprene from renewable resources. These methods may use one or more columns to remove volatile and/or bio-byproduct impurities resulting from fermentation.

We have determined methods of purifying isoprene in a fermentor off-gas generated from renewable resources using solvents (e.g., non-polar solvents) with absorption and stripping processes that may provide isoprene having significantly improved purity. The purified isoprene compositions described herein are particularly suitable for use in applications conventionally using petroleum-based isoprene, such as polymerization and use as a starting material in the synthesis of numerous desirable chemical compositions.

Accordingly, in one aspect is provided a method of purifying isoprene from a fermentor off-gas, comprising: contacting the fermentor off-gas with a solvent in a column to form: an isoprene-rich solution comprising the solvent and a major portion of the isoprene; and a vapor comprising a major portion of the volatile impurity. In some embodiments, the method further comprises: stripping isoprene from the isoprene-rich solution in a second column to form: an isoprene-lean solution comprising a major portion of the bio-byproduct impurity; and purified isoprene composition. Also provided are purified isoprene compositions.

Unless expressed otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "isoprene" refers to 2-methyl-1,3-butadiene (CAS# 78-79-5). Isoprene can be produced as the direct and final volatile C5 hydrocarbon product from the elimination of pyrophosphate from 3,3-dimethylallyl pyrophosphate (DMAPP), and does not involve the linking or polymerization of [an] IPP molecule(s) to [a] DMAPP molecule(s). The term "isoprene" is not generally intended to be limited to its method of production unless indicated otherwise herein.

As used herein, "biologically produced isoprene" or "bio-isoprene" refers to isoprene produced by any biological means, such as produced by genetically engineered cell cultures, natural microbials, plants or animals. A bioisoprene composition usually contains fewer hydrocarbon impurities than isoprene produced from petrochemical sources and often requires minimal treatment in order to be of polymerization grade. A bioisoprene composition also has a different impurity profile from a petrochemically produced isoprene composition.

While isoprene can be obtained by fractionating petroleum, the purification of this material is expensive and time-consuming. Petroleum cracking of the C5 stream of hydrocarbons produces only about 15% isoprene. Isoprene is also naturally produced by a variety of microbial, plant, and animal species. In particular, two pathways have been identified for the biosynthesis of isoprene: the mevalonate (MVA) pathway and the non-mevalonate (DXP) pathway. Genetically engineered cell cultures in bioreactors have produced isoprene more efficiently, in larger quantities, in higher purities and/or with unique impurity profiles, e.g., as described in International Patent Application Publication No. WO2009/076676; U.S. patent application Ser. Nos. 12/496,573, 12/560,390, 12/560,317, 12/560,370, 12/560,305, and 12/560,366; and U.S. provisional patent application Nos. 61/187,930, 61/187,934, and 61/187,959.

Crude bioisoprene compositions are distinguished from isoprene derived from petroleum (herein referred to as "petroisoprene") compositions in that bioisoprene compositions are substantially free of any contaminating unsaturated C5 hydrocarbons that are usually present in petroisoprene compositions, such as, but not limited to, 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, and cis-pent-3-ene-1-yne. If any contaminating unsaturated C5 hydrocarbons are present in the bioisoprene starting material composition described herein, they are present in lower levels than that in petroisoprene compositions. Crude bioIsoprene may have higher levels of certain C5 hydrocarbons than highly purified petroisoprene. Several of these impurities are particularly problematic given their structural similarity to isoprene and the fact that they can act as polymerization catalyst poisons. As detailed below, biologically produced isoprene compositions can be substantially free of any contaminating unsaturated C5 hydrocarbons without undergoing extensive purification.

Further, bioisoprene is distinguished from petroisoprene by carbon finger-printing. In one aspect, bioisoprene has a higher radioactive carbon-14 ($^{14}C$) content or higher $^{14}C/^{12}C$ ratio that petroisoprene. Bioisoprene is produced from renewable carbon sources, thus the $^{14}C$ content or the $^{14}C/^{12}C$ ratio in bioisoprene is the same as that in the present atmosphere. Petroisoprene, on the other hand, is derived from fossil fuels deposited thousands to millions of years ago, thus the $^{14}C$ content or the $^{14}C/^{12}C$ ratio is diminished due to radioactive decay. As discussed in greater detail herein, the fuel products derived from bioisoprene has higher $^{14}C$ content or $^{14}C/^{12}C$ ratio than fuel products derived from petroisoprene. In one embodiment, a fuel product derived from bioisoprene described herein has a $^{14}C$ content or $^{14}C/^{12}C$ ratio similar to that in the atmosphere. In another aspect, bioisoprene can be analytically distinguished from petroisoprene by the stable carbon isotope ratio ($^{13}C/^{12}C$), which can be reported as "delta values" represented by the symbol $\delta^{13}C$. For examples, for isoprene derived from extractive distillation of $C_5$ streams from petroleum refineries, $\delta^{13}C$ is about −22‰ to about −24‰. This range is typical for light, unsaturated hydrocarbons derived from petroleum, and products derived from petroleum-based isoprene typically contain isoprenic units with the same $\delta^{13}C$. Bioisoprene produced by fermentation of corn-derived glucose ($\delta^{13}C$-10.73‰) with minimal amounts of other carbon-containing nutrients (e.g., yeast extract) produces isoprene which can be polymerized into polyisoprene with $\delta^{13}C$-14.66‰ to −14.85‰. Products produced from such bioisoprene are expected to have $\delta^{13}C$ values that are less negative than those derived from petroleum-based isoprene.

Additionally, bioisoprene compositions are distinguished from petroisoprene composition in that bioisoprene compositions contain other bio-byproducts, for example comprising polar impurities, that are not present or present in much lower levels in petroisoprene compositions, such as alcohols, aldehydes, ketones and the like. The bio-byproduct may include, but is not limited to, ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol), citronellol (3,7-dimethyl-6-octen-1-ol) or a linear isoprene polymer (such as a linear isoprene dimer or a linear isoprene trimer derived from the polymerization of multiple isoprene units). As described herein, bioisoprene compositions may additionally comprise significant amounts of one or more volatile impurities (e.g., $O_2$, $N_2$, $H_2O$, $CO_2$) acquired during fermentation. Removal of one or more of these compounds (e.g., polar compounds and/or volatile impurities) from the bioisoprene as described in the methods herein may be desirable.

Unless defined otherwise based on the context in which it is used, "major portion" intends an amount greater than 50% (by weight). For example, a major portion of isoprene means more than 50% of the isoprene referenced. In some embodiments, major portion is greater than 60%, 70%, 75%, 80%, 90%, 95%, or 99%, by weight.

As used herein, a "purified isoprene composition" refers to an isoprene composition that has been separated from at least a portion of one or more components that are present in the fermentor off-gas (e.g., a portion of volatile impurity and/or bio-byproduct impurity). A purified isoprene composition may exist in any phase or mixture of phases, such as a complete gas phase (e.g., isoprene gas with one or more additional components), a complete liquid phase (e.g., a solution comprising isoprene with 0, 1, 2, or more components), a solid phase, or mixtures thereof. In some embodiments, the purified isoprene composition is at least about 20%, by weight, free from components other than isoprene. In various embodiments, the purified isoprene composition is at least or about 25%, 30%, 40%, 50%, 60%, 70%, 75%, 80%, 90%, 95%, 98% or 99%, by weight, pure. Purity can be assayed by any appropriate method, e.g., by column chromatography, HPLC analysis, or GC-MS analysis.

As used herein, "bio-byproduct" or "bio-byproduct impurity" refers to one or more organic compounds, excluding isoprene and methane, associated the biological fermentation processes and obtained together with isoprene in the referenced fermentor off-gas.

As used herein, "volatile impurity" means methane and/or one or more inorganic compounds found in the referenced fermentor off-gas in the gaseous state under standard atmospheric conditions.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used here. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

Isoprene Purification

Provided herein are methods of enriching and/or purifying isoprene. In some embodiments, the isoprene is from a fermentor off-gas. In one aspect is provided a method of purifying isoprene from a fermentor off-gas, wherein the off-gas comprises isoprene and volatile impurity. In one embodiment is provided a method of purifying isoprene from a fermentor off-gas, wherein the off-gas comprises isoprene and volatile impurity, the method comprising: contacting the fermentor off-gas with a solvent in a column to form: an isoprene-rich solution comprising the solvent and a major portion of the isoprene; and a vapor comprising a major portion of the volatile impurity.

In one aspect is provided a method of purifying isoprene from a solution comprising isoprene and bio-byproduct impurity. In one embodiment is provided a method of purifying isoprene from a solution comprising isoprene and bio-byproduct impurity, the method comprising: stripping isoprene from the solution in a column to form: an isoprene-lean solution comprising a major portion of the bio-byproduct impurity; and a purified isopene composition.

In one aspect is provided a method of purifying isoprene from a fermentor off-gas, wherein the off-gas comprises isoprene, volatile impurity, and bio-byproduct impurity, the method comprising: (a) contacting the fermentor off-gas with a solvent in a first column to form: an isoprene-rich solution comprising the solvent, a major portion of the isoprene and a major portion of the bio-byproduct impurity; and a vapor comprising a major portion of the volatile impurity; (b) transferring the isoprene-rich solution from the first column to a second column; and (c) stripping isoprene from the isoprene-rich solution in the second column to form: an isoprene-lean solution comprising a major portion of the bio-byproduct impurity; and a purified isopene composition.

FIG. 1 illustrates an exemplary method of purifying isoprene and an exemplary apparatus. Fermentor off-gas comprising isoprene may be generated from renewable resources (e.g., carbon sources) by any method in the art for example, as described in U.S. provisional patent application No. 61/187, 944, the content of which is hereby incorporated by reference, particularly with respect to the methods of generating fermentor off-gas comprising isoprene. The fermentor off-gas generated from one or more individual fermentors 12 (e.g., 1, 2, 3, 4, 5, 6, 7, 8, or more fermentors connected in series and/or in parallel) may be directed to a first column 14. As described below, the fermentor off-gas may be directed through an isolation unit 16 and/or compressed by a compression means, such as compression system 18. Additionally, the temperature of the fermentor off-gas may optionally be reduced at any point, for example, to form a condensate or partial condensate prior to contact with the solvent (which may aid in solubilization of one or more off-gas components, such as isoprene). The fermentor off-gas may be contacted (e.g., absorbed) at column 14 with a solvent (e.g., any solvent described herein, such as a non-polar high boiling-point solvent). The volatile impurities having less propensity for absorption in the solvent (particularly with non-polar high boiling-point solvents) are separated from the remaining solvent/fermentor off-gas mixture, resulting in a vapor comprising a major portion of the volatile impurity (e.g., exiting at port 20), and an isoprene-rich solution having a major portion of the isoprene and a major portion of the bio-byproduct impurity (e.g., at port 22). A stripping vapor flow may be provided by any suitable means (e.g., by steam injection or a reboiler unit 23 below the fermentor off-gas feed point in the first column), which may aid in separation of the volatile impurity from the remaining solution. Steam may be directed through the column (at any suitable location, shown in FIG. 1) to provide a sweeping vapor phase which may aid in the removal of the volatile impurity.

The isoprene-rich solution having a major portion of the isoprene and a major portion of the bio-byproduct impurity (e.g., at port 22) may be directed to a second column 24. The second column may be isolated from the first column 14 (as shown in FIG. 1) or may be part of a single column comprising both the first and second columns (e.g., a tandem column wherein the solvent enters the first column at or near one end, and exits the second column at or near an opposite end). The isoprene may be stripped from the isoprene-rich solution in the second column to generate a purified isopene composition (e.g., at port 26) and an isoprene-lean solution comprising a major portion of the bio-byproduct impurity (e.g., at port 28). Steam may be added to the second column, which may aid in stripping of the isoprene from the remaining solution. Steam may be directed through the column (at any suitable location, such as the opposite end of the entry point of the isoprene-rich solution and/or the near the end of the isoprene-lean solution exit as shown in FIG. 1).

As described herein, the columns may be conventional and of any suitable size. Exemplary types of columns are commercially available from manufacturers including Koch Modular Process Systems (Paramus, N.J.), Fluor Corporation (Irving, Tex.), Kuhni USA (Mount Holly, N.C.). In general, columns are designed to maximize vapor/liquid contact in order to achieve the desired efficiency. This is achieved by filling the column with either a packing material, or trays spaced at regular intervals along the column. Suitable packing materials include both random and structured types based on metal, glass, polymer and ceramic materials. Exemplary random packing types include Raschig rings, Pall rings, A-PAK rings, Saddle rings, Pro-Pak, Heli-Pak, Ceramic saddles and FLEXIRINGS®. Structured packings include wire mesh and perforated metal plate type materials. Manufacturers specializing in column packings include ACS Separations & Mass-Transfer Products (Houston, Tex.), Johnson Bros. Metal Forming Co. (Berkeley, Ill.) and Koch Glitsch, Inc. Knight Div. (East Canton, Ohio). The efficiency of a gas stripping column is expressed in terms of the theoretical plate height and the total number of plates in the column. In general, the greater the number of theoretical plates present, the greater the efficiency of the column. Laboratory scale columns can be purchased from Ace Glass (Vineland, N.J.), Sigma-Aldrich (St. Louis, Mo.) and Chemglass (Vineland, N.J.). Suitable types of glass column include Vigreux, Snyder, Hemple and Perforated-plate type columns. Columns can include packing materials, or contain features designed to maximize vapor/liquid contact. A laboratory scale gas scrubber unit (part # CG-1830-10) is available from Chemglass and consists of a packed glass column, solvent reservoir and solvent recirculation pump.

The purified isoprene composition from the second column 24 (e.g., exiting at port 26) may be further purified by any suitable means (e.g., by using a reflux condenser 34 and/or an adsorption system 36, such as a silica adsorption system). The reflux reduces the solvent composition in the isoprene product. The isoprene-lean solution may be recycled back to the first column for reuse (e.g., as shown in FIG. 1 at port 30). The isoprene-lean solution may be purified by any suitable means (e.g., by liquid-liquid extraction and/or an adsorption system 32, such as a silica adsorption system) prior to recycling to the first column 14 to reduce to amount of bio-byproduct. Additionally, the temperature of the isoprene-lean solution may be reduced by any suitable means prior to recycling to the first column 14 (e.g., prior to, simultaneously, and/or after optionally purifying the isoprene solution). FIG. 1 shows an example of reducing the temperature of the isoprene-lean solution at port 40 prior to purification of the isoprene-lean solution (in this case, using coolant for temperature reduction).

In one embodiment, a cooler unit is coupled immediately downstream of system 32 to provide additional cooling. Further, the lean isoprene-solvent from the second column 24 may be phase separated to remove water, before the solution is chilled and returned to the top of the first column 14; this phase separation unit would be coupled immediately below port 40. Further, the condensed water and isoprene from condenser 34 may be similarly phase separated to remove water by a similar phase separator unit coupled immediately downstream of condenser 34. Thereby only the isoprene phase is returned back to the second column. In each case, the water from the phase separation units is a waste stream.

The vapor comprising a major portion of the volatile impurity (e.g., the vapor exiting at port 20 in FIG. 1) may comprise a minor portion of isoprene (e.g., residual isoprene not remaining in the isoprene-rich solution). The residual isoprene may be recollected for use from the vapor comprising a major portion of the volatile impurity by any suitable means (e.g., an adsorption system 38, such as an activated carbon adsorption system) and in some cases, as shown in FIG. 1, may be combined with the purified isoprene composition (e.g., prior to, during, or after additional purification, such as an adsorption system similar to system 36). FIG. 1 also shows an optional capture device 42 (e.g., a thermal oxidizer and/or $CO_2$ capture system) capable of reducing the amount of undesirable components released into the atmosphere (e.g., $CO_2$) from the vapor.

Fermentor Off-Gas

Techniques for producing fermentor off-gas comprising isoprene that may be used in the methods herein are described in, for example, International Patent Application Publication No. WO2009/076676; U.S. patent application Ser. Nos. 12/496,573, 12/560,390, 12/560,317, 12/560,370, 12/560,305, and 12/560,366; and U.S. provisional patent application Nos. 61/187,930, 61/187,934, and 61/187,959. In particular, these compositions and methods increase the rate of isoprene production and increase the amount of isoprene that is produced.

As described in more detail below, the fermentor off-gas may be produced by cells in culture. In some embodiments, the cells in culture are capable of producing greater than about 400 nmole of isoprene/gram of cells for the wet weight of the cells/hour (nmole/$g_{wcm}$/hr) of isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

Materials and methods suitable for the maintenance and growth of bacterial cultures are well known in the art. Exemplary techniques may be found in Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass., which are each hereby incorporated by reference in their entireties, particularly with respect to cell culture techniques.

Standard cell culture conditions can be used to culture the cells (see, for example, International Patent Publication WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, the cells in culture are capable of converting more than about 0.002% of the carbon in a cell culture medium into isoprene. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the cells in culture comprise a heterologous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In some embodiments, the cells in culture are capable of producing an amount of isoprene (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the cells in culture are capable of producing isoprene only in stationary phase. In some embodiments, the cells in culture are capable of producing isoprene in both the growth phase and stationary phase. In various embodiments, the cells in culture are capable of producing an amount of isoprene during stationary phase is greater than or about 2, 3, 4, 5, 10, 20, 30, 40, 50, or more times the amount of isoprene produced during the growth phase for the same length of time.

In some embodiments, the cells in culture are from a system that includes a reactor chamber wherein the cells are capable of producing greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In some embodiments, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects, the cells in culture further comprise a heterologous nucleic acid encoding an IDI polypeptide. In some embodiments, the cells further comprise an insertion of a copy of an endogenous nucleic acid encoding an IDI polypeptide. In some embodiments, the cells further comprise a heterologous nucleic acid encoding a DXS polypeptide. In some embodiments, the cells further comprise an insertion of a copy of an endogenous nucleic acid encoding a DXS polypeptide. In some embodiments, the cells further comprise one or more nucleic acids encoding an IDI polypeptide and a DXS polypeptide. In some embodiments, one nucleic acid encodes the isoprene synthase polypeptide, IDI polypeptide, and DXS polypeptide. In some embodiments, one vector encodes the isoprene synthase polypeptide, IDI polypeptide, and DXS polypeptide. In some embodiments, the vector comprises a selective marker, such as an antibiotic resistance nucleic acid.

In some embodiments, the heterologous isoprene synthase nucleic acid is operably linked to a T7 promoter, such as a T7 promoter contained in a medium or high copy plasmid. In some embodiments, the heterologous isoprene synthase nucleic acid is operably linked to a Trc promoter, such as a Trc promoter contained in a medium or high copy plasmid. In some embodiments, the heterologous isoprene synthase nucleic acid is operably linked to a Lac promoter, such as a Lac promoter contained in a low copy plasmid. In some embodiments, the heterologous isoprene synthase nucleic acid is operably linked to an endogenous promoter, such as an endogenous alkaline serine protease promoter. In some embodiments, the heterologous isoprene synthase nucleic acid integrates into a chromosome of the cells without a selective marker.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments, at least a portion of the cells in culture maintain the heterologous isoprene synthase nucleic acid for at least or about 5, 10, 20, 40, 50, 60, 65, or more cell divisions in a continuous culture (such as a continuous culture without dilution). In some embodiments, the nucleic acid comprising the isoprene synthase, IDI, or DXS nucleic acid also comprises a selective marker, such as an antibiotic resistance nucleic acid.

In some embodiments, the cells in culture further comprise a heterologous nucleic acid encoding an MVA pathway polypeptide (such as an MVA pathway polypeptide from *Saccharomyces cerevisia* or *Enterococcus faecalis*). In some embodiments, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments, the cells comprise an isoprene synthase, DXS, and MVA pathway nucleic acid. In some embodiments, the cells comprise an isoprene synthase nucleic acid, a DXS nucleic acid, an IDI nucleic acid, and a MVA pathway nucleic (in addition to the IDI nucleic acid).

In some embodiments, the isoprene synthase polypeptide is a naturally-occurring polypeptide from a plant such as *Pueraria* (e.g., *Pueraria montana* or *Pueraria lobata*).

In some embodiments, the cells in culture are bacterial cells, such as gram-positive bacterial cells (e.g., *Bacillus* cells such as *Bacillus subtilis* cells or *Streptomyces* cells such as *Streptomyces lividans*, *Streptomyces coelicolor*, or *Strepto-*

*myces griseus* cells). In some embodiments, the cells in culture are gram-negative bacterial cells (e.g., *Escherichia* cells such as *Escherichia coli* cells or *Pantoea* cells such as *Pantoea citrea* cells). In some embodiments, the cells in culture are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments, the microbial polypeptide carbon source includes one or more polypeptides from yeast or bacteria. In some embodiments, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

As previously mentioned, the fermentor off-gas described herein may be derived from renewable resources (e.g., carbon sources, biological and/or plant). Exemplary renewable resources are described in, for example, U.S. provisional patent application Nos. 61/187,944 (the content of which is hereby incorporated by reference), and include cheese whey permeate, cornsteep liquor, sugar beet molasses, barley malt, and components from any of the foregoing. Exemplary renewable carbon sources also include acetate, glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments of the methods described herein, the fermentor off-gas is derived from renewable resources. In some embodiments, the fermentor off-gas comprises bioisoprene. In some embodiments, the fermentor off-gas comprises greater than or about 98.0, 98.5, 99.0, 99.5, or 100% isoprene by weight compared to the weight of all C5 hydrocarbons in the fermentor off-gas. In some embodiments, the fermentor off-gas comprises greater than or about 99.90, 99.92, 99.94, 99.96, 99.98, or 100% isoprene by weight compared to the weight of all C5 hydrocarbons in the fermentor off-gas. In some embodiments, the fermentor off-gas produces a relative detector response of greater than or about 98.0, 98.5, 99.0, 99.5, or 100% for isoprene compared to the detector response for all C5 hydrocarbons in the fermentor off-gas when analyzed by gas chromatography with flame ionization detection (GC/FID). In some embodiments, the fermentor off-gas produces a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the fermentor off-gas when analyzed similarly. In some embodiments, the fermentor off-gas comprises between about 98.0 to about 98.5, about 98.5 to about 99.0, about 99.0 weight of all C5 hydrocarbons in the fermentor off-gas. In some embodiments, the fermentor off-gas comprises between about 99.90 to about 99.92, about 99.92 to about 99.94, about 99.94 to about 99.96, about 99.96 to about 99.98, about 99.98 to 100% isoprene by weight compared to the weight of all C5 hydrocarbons in the fermentor off-gas.

In some embodiments of the methods described herein, the fermentor off-gas comprises less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 2-methyl-2-butene, 3-methyl-1-butyne, pent-4-ene-1-yne, trans-pent-3-ene-1-yne, or cis-pent-3-ene-1-yne) by weight compared to the weight of all C5 hydrocarbons in the fermentor off-gas. In some embodiments, the fermentor off-gas has a relative detector response of less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the fermentor off-gas. In some embodiments, the fermentor off-gas has a relative detector response of less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne compared to the detector response for all C5 hydrocarbons in the fermentor off-gas. In some embodiments, the highly pure isoprene starting composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne) by weight compared to the total weight of all C5 hydrocarbons in the fermentor off-gas.

In some embodiments of the methods described herein, the fermentor off-gas comprises less than or about 50, 40, 30, 20, 10, 5, 1, 0.5, 0.1, 0.05, 0.01, or 0.005 µg/L of a compound that inhibits the polymerization of isoprene for any compound in the fermentor off-gas that inhibits the polymerization of isoprene. In some embodiments, the fermentor off-gas comprises between about 0.005 to about 50, such as about 0.01 to about 10, about 0.01 to about 5, about 0.01 to about 1, about 0.01 to about 0.5, or about 0.01 to about 0.005 µg/L of a compound that inhibits the polymerization of isoprene for any compound in the fermentor off-gas that inhibits the polymerization of isoprene. In some embodiments, the fermentor off-gas comprises less than or about 50, 40, 30, 20, 10, 5, 1, 0.5, 0.1, 0.05, 0.01, or 0.005 µg/L of a hydrocarbon other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne). In some embodiments, the fermentor off-gas comprises between about 0.005 to about 50, such as about 0.01 to about 10, about 0.01 to about 5, about 0.01 to about 1, about 0.01 to about 0.5, or about 0.01 to about 0.005 µg/L of a hydrocarbon other than isoprene. In some embodiments, the fermentor off-gas comprises less than or about 50, 40, 30, 20, 10, 5, 1, 0.5, 0.1, 0.05, 0.01, or 0.005 µg/L of a protein or fatty acid (such as a protein or fatty acid that is naturally associated with natural rubber).

In some embodiments of the methods described herein, the fermentor off-gas comprises less than or about 10, 5, 1, 0.8, 0.5, 0.1, 0.05, 0.01, or 0.005 ppm of alpha-acetylenes, piperylenes, acetonitrile, or 1,3-cyclopentadiene. In some embodiments, the fermentor off-gas comprises less than or about 5, 1, 0.5, 0.1, 0.05, 0.01, or 0.005 ppm of sulfur or allenes. In some embodiments, the fermentor off-gas comprises less than or about 30, 20, 15, 10, 5, 1, 0.5, 0.1, 0.05, 0.01, or 0.005 ppm of all acetylenes (such as 1-pentyne, 2-pentyne, 3-methyl-1-butyne, pent-4-ene-1-yne, trans-pent-3-ene-1-yne, and cis-pent-3-ene-1-yne). In some embodiments, the fermentor off-gas comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimers (e.g., cyclic C10 compounds derived from the dimerization of two isoprene units).

Off-Gas Bio-Byproduct Impurity

The bio-byproduct of the fermentor off-gas may comprise any one or any combination of compounds described herein. In some embodiments, the bio-byproduct of the fermentor off-gas comprises one or more polar compounds. Polarity can be determined by methods known in the art, for example by measuring water solubility, potential for hydrogen bonding, dielectric constant and/or an oil/water partition coefficient. In some embodiments, one or more compounds of the bio-byproduct has an overall polarity greater than the polarity of isoprene, e.g., as measured by having a dielectric constant greater than 2.1 at 25° C. (77° F.). In some embodiments, greater than about any of 20%, 30%, 50%, 60%, 70%, 80%, 90%, or 95% (w/w) of the bio-byproduct is comprised of one or more compounds having an overall polarity greater than the polarity of isoprene. In some embodiments, one or more of the compounds of the bio-byproduct has a dielectric constant of greater than about 2, or greater than about 3, or greater than about 5, or greater than about 7.5, or greater than about 10 at 20° C. In some embodiments, greater than about any of 20%, 30%, 50%, 60%, 70%, 80%, 90%, or 95% (w/w) of the bio-byproduct is comprised of one or more compounds having a dielectric constant of greater than about 2, or greater than about 3, or greater than about 5, or greater than about 7.5, or greater than about 10 at 20° C.

In some embodiments, the fermentor off-gas includes one or more of the following compounds in the bio-byproduct: an alcohol, an aldehyde, or a ketone (such as any of the alcohols, aldehydes, or ketones described herein). In some embodiments, the fermentor off-gas includes (i) an alcohol and an aldehyde, (ii) an alcohol and a ketone, (iii) an aldehyde and a ketone, (iv) an alcohol, an aldehyde, and a ketone, or (v) esters.

The fermentor off-gas may comprise any one or any combination of one of more of the following compounds in the bio-byproduct: ethanol, acetone, methanol, acetaldehyde, methacrolein, methyl vinyl ketone, 2-methyl-2-vinyloxirane, 3-methylfuran, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, 3-hexen-1-ol, 3-hexen-1-yl acetate, limonene, geraniol (trans-3,7-dimethyl-2,6-octadien-1-ol), citronellol (3,7-dimethyl-6-octen-1-ol).

In some embodiments, the fermentor off-gas includes any one or any combination of one of more of the following compounds in the bio-byproduct: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In some embodiments, the fermentor off-gas comprises one or more of the following compounds in the bio-byproduct: ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol).

In some embodiments of the methods described herein, the fermentor off-gas comprises greater than or about 0.005, 0.01, 0.05, 0.1, 0.5, 1, 5, 10, 20, 30, 40, 60, 80, 100, or 120 µg/L of bio-byproduct (e.g., bio-byproduct comprising one or more compounds selected from ethanol, acetone, methanol, acetaldehyde, methacrolein, methyl vinyl ketone, 3-methylfuran, 2-methyl-2-vinyloxirane, cis- and trans-3-methyl-1,3-pentadiene, and a C5 prenyl alcohol (such as 3-methyl-3-buten-1-ol or 3-methyl-2-buten-1-ol)). In some embodiments, the fermentor off-gas comprises greater than or about 0.005, 0.01, 0.05, 0.1, 0.5, 1, 5, 10, 20, 30, 40, 60, 80, 100, or 120 µg/L of one or more compounds in the bio-byproduct (e.g., one or more compounds selected from ethanol, acetone, methanol, acetaldehyde, methacrolein, methyl vinyl ketone, 3-methylfuran, 2-methyl-2-vinyloxirane, cis- and trans-3-methyl-1,3-pentadiene, and a C5 prenyl alcohol (such as 3-methyl-3-buten-1-ol or 3-methyl-2-buten-1-ol)). In some embodiments, the fermentor off-gas comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 µg/L of bio-byproduct (e.g., bio-byproduct comprising one or more compounds selected from ethanol, acetone, methanol, acetaldehyde, methacrolein, methyl vinyl ketone, 3-methylfuran, 2-methyl-2-vinyloxirane, cis- and trans-3-methyl-1,3-pentadiene, and a C5 prenyl alcohol (such as 3-methyl-3-buten-1-ol or 3-methyl-2-buten-1-ol)). In some embodiments, the fermentor off-gas comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 µg/L of one or more compounds of the bio-byproduct (e.g., one or more compounds selected from ethanol, acetone, methanol, acetaldehyde, methacrolein, methyl vinyl ketone, 3-methylfuran, 2-methyl-2-vinyloxirane, cis- and trans-3-methyl-1,3-pentadiene, and a C5 prenyl alcohol (such as 3-methyl-3-buten-1-ol or 3-methyl-2-buten-1-ol)).

In various embodiments of the methods described herein, the amount of bio-byproduct and/or the amount of one or more compounds of the bio-byproduct relative to amount of isoprene in units of percentage by weight (i.e., weight of the bio-byproduct divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the bio-byproduct and/or one or more compounds of the bio-byproduct compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of bio-byproduct and/or the amount of one or more compounds of the bio-byproduct relative to amount of isoprene in units of percentage by weight (i.e., weight of the bio-byproduct or weight of the one or more compounds divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, the fermentor off-gas contains one or more of the following compounds in the bio-byproduct: methanol, ethanol, methanethiol, 1-butanol, 3-methyl-1-propanol, acetone, acetic acid, 2-butanone, 2-methyl-1-butanol, or indole. In some embodiments, the fermentor off-gas contains 1 ppm or more of one or more of the following compounds: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of bio-byproduct and/or one or more compounds of the bio-byproduct (e.g., of one or more of the following: methanol, acetaldehyde, ethanol, methanethiol, 1-butanol, 3-methyl-1-propanol, acetone, acetic acid, 2-butanone, 2-methyl-1-butanol, or indole) is between about 1 to about 10,000 ppm in the fermentor off-gas. In some embodiments, the fermentor off-gas includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. In some embodiments, the amount of bio-byproduct in the fermentor off-gas is at a concentration from between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. Bio-byproduct from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology,* 74(7):2179-2186, 2008 which is hereby incorporated by reference in its entirety, particular with respect to the analysis of volatile organic compounds).

Off-Gas Volatile Impurity

The optimal ranges of various components during the fermentation of isoprene to achieve suitable production levels and safe operation (e.g., based on flammability characteristics) is described in, for example, U.S. provisional patent application No. 61/187,944, the content of which is hereby incorporated by reference. As a result, the fermentation off-gas may contain volatile impurity (e.g., volatile impurity comprising water vapor, $CO_2$, $N_2$, and $O_2$). Removing this volatile impurity from isoprene may be desirable prior to commercial use. Accordingly, in one aspect, the methods described herein decrease or remove volatile impurity from isoprene fermentor off-gas.

In some embodiments, the volatile impurity from fermentor off-gas includes one, two, or more compounds selected from $H_2O$, $CO_2$, CO, $N_2$, $CH_4$, $H_2$, and $O_2$. In some embodiments, the volatile impurity comprises $H_2O$, $CO_2$, and $N_2$. In some embodiments, the volatile impurity comprises $H_2O$, $CO_2$, $N_2$, and $O_2$. In some embodiments, the volatile impurity comprises an inorganic gas at standard temperature and pressure.

In some embodiments, the fermentor off-gas comprises volatile impurity (e.g., wherein the volatile impurity comprises a compound such as $H_2O$, $CO_2$, CO, $N_2$, $CH_4$, $H_2$, and/or $O_2$) at a level of at least about 2, 5, 10, 50, 75, or 100-fold less than the amount of isoprene. In some embodiments, the volatile impurity of the fermentor off-gas comprises one or more compounds (e.g., $H_2O$, $CO_2$, CO, $N_2$, $CH_4$, $H_2$, and/or $O_2$) at a level of at least about 2, 5, 10, 50, 75, or 100-fold less than the amount of isoprene. In some embodiments, the portion off-gas other than isoprene comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% (volume) oxygen. In some embodiments, the portion of off-gas other than isoprene comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% (volume) nitrogen. In some embodiments, the portion of off-gas other than isoprene comprises between about 0% to about 99% (volume) $H_2O$, such as between about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% (volume) $H_2O$. In some embodiments, the portion off-gas other than isoprene comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, the volatile impurity of the fermentor off-gas comprises about 10 to about 90, or about 20 to about 80, or about 40 to about 60, or about 10 to about 20, or about 20 to about 30, or about 30 to about 40, or about 40 to about 50, or about 50 to about 60, or about 60 to about 70, or about 70 to about 80, or about 80 to 90, or about 90 to about 99 mol % $N_2$. In some embodiments, the volatile impurity comprises about 10 to about 90, or about 20 to about 80, or about 40 to about 60, or about 10 to about 20, or about 20 to about 30, or about 30 to about 40, or about 40 to about 50, or about 50 to about 60, or about 60 to about 70, or about 70 to about 80 or about 90, or about 90 to about 99 mol % carbon dioxide. In some embodiments, the volatile impurity comprises about 10 to about 90, or about 20 to about 80, or about 40 to about 60, or about 10 to about 20, or about 20 to about 30, or about 30 to about 40, or about 40 to about 50, or about 50 to about 60, or about 60 to about 70, or about 70 to about 80 or about 90, or about 90 to about 99 mol % carbon monoxide. In some embodiments, the volatile impurity comprises about 10 to about 90, or about 20 to about 80, or about 40 to about 60, or about 10 to about 20, or about 20 to about 30, or about 30 to about 40, or about 40 to about 50, or about 50 to about 60, or about 60 to about 70, or about 70 to about 80 or about 90, or about 90 to about 99, or less than 50, or less than 40, or less than 30, or less than 20, or less than 10, or less than 5, or zero, or greater than 80, or greater than 90, or greater than 95 mol % $O_2$. In some embodiments, the volatile impurity comprises about 10 to about 90, or about 20 to about 80, or about 40 to about 60, or about 10 to about 20, or about 20 to about 30, or about 30 to about 40, or about 40 to about 50, or about 50 to about 60, or about 60 to about 70, or about 70 to about 80 or about 90, or about 90 to about 99 mol % hydrogen. In some embodiments, the volatile impurity comprises less than about 50, or less than about 40, or less than about 30, or less than about 20, or less than about 10, or less than about 5, or less than about 3 mol % methane.

In some embodiments, the volatile impurity of the fermentor off-gas comprises about 25 to about 80 mol % $CO_2$, about 45 to about 99 mol % $N_2$, and optionally comprises less than about 50 mol % $O_2$. In some embodiments, the volatile impurity comprises about 40 to about 60 mol % $CO_2$, about 65 to about 99 mol % $N_2$, and optionally comprises less than about 25 mol % $O_2$.

Although the fermentor off-gas derived from renewable resources originates from fermentation in the gas phase, the off-gas may exist as described herein in any phase or mixture of phases, such as a complete gas phase, in a partial gas phase and partial liquid phase (such as a condensate), or in a complete liquid phase. In some embodiments, at least a portion of the fermentor off-gas derived from renewable resources is in a gas phase. In some embodiments, at least a portion of the fermentor off-gas derived from renewable resources is in a liquid phase (such as a condensate). In some embodiments, at least a portion of the fermentor off-gas derived from renewable resources is in a solid phase. In some embodiments, the fermentor off-gas has undergone one or more purification steps prior to use in the methods described herein. In some embodiments, the fermentor off-gas has not undergone purification prior to use in the methods described herein. In some embodiments, at least a portion of the fermentor off-gas derived from renewable resources is absorbed to a solid support, such as a support that includes silica and/or activated carbon prior to use in the methods described herein. In some embodiments, the fermentor off-gas is mixed with one or more solvents prior to use in the methods described herein. In some embodiments, the fermentor off-gas is mixed with one or more gases prior to use in the methods described herein.

In some embodiments of the methods described herein, the temperature of the fermentor off-gas is reduced prior to contacting the solvent in the first column. Temperature reduction of the fermentor off-gas may aid in solubilization of one or more off-gas components (such as isoprene) in the solvent (e.g., a high boiling point hydrophobic solvent). The temperature may be reduced by any suitable means (e.g., use of a coolant). In some embodiments, the temperature reduction of the fermentor off-gas results in a partial or complete condensation of the fermentor off-gas. In some embodiments, the temperature of the fermentor off-gas is reduced to less than any of about 95%, 90%, 80%, 70%, 60%, 50%, 40%, 30%, 20%, or 10% of the off-gas temperature in ° C. from the fermentor(s). In some embodiments, the temperature of the fermentor off-gas is reduced to less than any of about 150° C., 125° C., 100° C., 90° C., 80° C., 70° C., 60° C., 50° C., 45° C., 40° C., 35° C., 30° C., 25° C., 20° C., 15° C., 10° C., 5° C., or 0° C. In some embodiments, the temperature of the fermentor off-gas is reduced to any of about 0° C. to about 150° C., 0° C. to about 125° C., about 0° C. to about 100° C., about 0° C. to about 75° C., about 0° C. to about 30° C., about 0° C. to about 20° C., about 0° C. to about 10° C., about 0° C. to about 7.5° C., or about 5° C.

In some embodiments of the methods described herein, the pressure of the fermentor off-gas is increased prior to contacting the solvent in the first column. The pressure may be increased by any suitable means (e.g., compression systems known in the art). Increased pressure may aid in solubilization of one or more off-gas components (such as isoprene) in the solvent (e.g., a high boiling point hydrophobic solvent). In some embodiments, the pressure of the fermentor off-gas is increased by more than any of about 10%, 20%, 30%, 40%, 50%, 60%, 70%, 80%, 90%, or 95% of the off-gas pressure (in PSIA—pounds per square inch absolute) from the fermentor(s). In some embodiments, the pressure of the fermentor off-gas is increased to more than any of about 10 PSIA, 20 PSIA, 30 PSIA, 40 PSIA, 50 PSIA, 60 PSIA, 70 PSIA, 80 PSIA, 90 PSIA, 100 PSIA, 110 PSIA, 120 PSIA, 130 PSIA, 140 PSIA, or 150 PSIA. In some embodiments, the pressure of the fermentor off-gas is increased to any of about 5 PSIA to about 150 PSIA, about 10 PSIA to about 100 PSIA, about 15 PSIA to about 75 PSIA, about 20 PSIA to about 65 PSIA, about 25 PSIA to about 60 PSIA, about 30 PSIA to about 50 PSIA, or about 35 PSIA to about 45 PSIA.

Isolation Unit

The fermentor off-gas may be routed through an isolation unit prior to reaching a column. The isolation unit may serve to prevent the fermentation process from being influenced by the downstream purification process. Additionally, the isolation unit may serve to provide a stable intermediate pressure to the column (e.g., with a make-up flow of recycle gas stream, fresh atmospheric air and/or other added gas, such as nitrogen). Foam-out and entrained liquid (e.g., media) may also be collected by the isolation unit and prevented from reaching the column. In some embodiments of any of the methods described herein, the fermentor off-gas is transferred to an isolation unit (the same or different isolation unit) prior to contacting the fermentor off-gas with the solvent in the first column. In some of these embodiments, the isolation unit is capable of stabilizing the off-gas pressure.

Solvents

Any suitable solvent may be used in the methods described herein. The solvent may be a pure solvent or a mixture of two or more solvents. In some instances, the solvent is capable of absorbing a major portion of the isoprene from the fermentor off-gas (or a major portion of the isoprene and a major portion of the bio-byproduct) and is not capable of absorbing a major portion of the volatile impurity of the fermentor off-gas under the same conditions. In some embodiments of the methods described herein, the solvent is capable of absorbing greater than about 2, 5, 10, 20, 50, 100, 200 or 500 times more isoprene (w/w) compared to the volatile impurity under the same conditions. In some embodiments of the methods described herein, the solvent is capable of only a relatively low $CO_2$ absorption (e.g., as defined by its Ostwald Coefficient). Accordingly, in some embodiments, the solvent is a low carbon dioxide absorption solvent. As used herein, unless otherwise stated, a "low carbon dioxide absorption solvent" intends a solvent having an Ostwald Coefficient of less than 2 at 130° F. and standard pressure. In some embodiments, the solvent is a low carbon dioxide absorption solvent having a $CO_2$ Ostwald coefficient of less than about any of about 1.75, about 1.5, about 1.25, about 1.1, or about 1.0 at 54° C. (130° F.) and at standard pressure.

The solvent may have a relatively high-boiling point. As used herein, unless otherwise stated, a "high boiling point solvent" intends a solvent having a boiling point of greater than 121° C. (250° F.) at 1 atm. In some embodiments of the methods described herein, the solvent is a high boiling point solvent with a boiling point of greater than about 121° C.

(250° F.), greater than about 135° C. (275° F.), greater than about 149° C. (300° F.), greater than about 163° C. (325° F.), greater than about 121° C. (350° F.), greater than about 191° C. (375° F.), or greater than about 204° C. (400° F.), or greater than about 177° C. (420° F.), or greater than about 232° C. (450° F.), or greater than about 246° C. (475° F.) at 1 atm. In some embodiments, the solvent has a boiling point from about 121° C. (250° F.) to about 149° C. (300° F.), or 135° C. (275° F.) to about 163° C. (325° F.), or about 149° C. (300° F.) to about 177° C. (350° F.), or about 163° C. (325° F.) to about 149° C. (375° F.), or about 135° C. (350° F.) to about 204° C. (400° F.), or about (191° C. (375° F.) to about (218° C. (425° F.), or about 204° C. (400° F.) to about 232° C. (450° F.), or about 218° C. (425° F.) to about 246° C. (475° F.) at 1 atm.

In some embodiments of the methods described herein, the solvent is relatively non-polar. The polarity of the solvent can be determined by any method known in the art (e.g., water solubility, potential for hydrogen bonding, dielectric constant and/or an oil/water partition coefficient). In some embodiments, the solvent is a non-polar solvent. As used herein, unless otherwise stated, a "non-polar solvent" intends a solvent having a dielectric constant of less than 15 at 20° C. In some embodiments, the solvent is a non-polar solvent having a dielectric constant of less than about 12, or less than about 10, or less than about 7.5, or less than about 5, or less than about 3, or less than about 2, or less than about 1 at 20° C. In some embodiments, the solvent has a solubility in water of less than about 5%, or less than about 3%, or less than about 2%, or less than about 1%, or less than about 0.5%, or less than about 0.25%, or less than about 0.1%, or less than about 0.05%, or less than about 0.025% under standard conditions.

The solvent used in the methods described herein, may be characterized by its Kauri-butanol value ("Kb value") as measured in the art. In some embodiments of the methods described herein, the solvent has a Kb value of less than 75, or less than 50, or less than 40, or less than 30, or less than 20, or less than 10. In some embodiments, the solvent has a Kb value from about 10 to about 40, or about 15 to about 35, or about 20 to about 30, or from about 23 to about 27, or about 25.

The solvent used in the methods described herein, may be characterized by its Aniline Point as measured in the art. In some embodiments of the methods described herein, the solvent has an Aniline Point of greater than about 52° C. (125° F.), or greater than about 66° C. (150° F.), or greater than about 79° C. (175° F.), or greater than about 91° C. (200° F.). In some embodiments, the solvent has an Aniline Point from about 66° C. (150° F.) to about 121° C. (250° F.), or from about 79° C. (175° F.) to about 93° C. (200° F.), or from about 82° C. (180° F.) to about 91° C. (195° F.).

The solvent used in the methods described herein, may be characterized by its Kinematic viscosity as measured in the art. In some embodiments of the methods described herein, the solvent has a Kinematic viscosity at 40° C. or less than about 3, or less than about 2.75, or less than about 2.25, or less than about 2.0, or less than about 1.75, or less than about 1.5, or less than about 1.25 centistokes (cSt).

The solvent used in the methods described herein, may be characterized by its surface tension as measured in the art. In some embodiments of the methods described herein, the solvent has a surface tension at 25° C. from about 15 to about 35 dyne/cm, or about 17 to about 32 dyne/cm, or about 20 to about 30 dyne/cm, or about 23 to about 27 dyne/cm, or about 25 dyne/cm.

The solvent used in the methods described herein, may be characterized by its molecular weight (or a weighted average molecular weight in the case of a mixed solvent system). In some embodiments of the methods described herein, the solvent has an average molecular weight from about 100 to about 250, or about 125 to about 225, or about 140 to about 200, or about 150 to about 175.

The solvent used in the methods described herein may have any one or combination of two or more of the properties described herein. For example, in some embodiments, the solvent used in the methods described herein may be a non-polar, high-boiling point solvent (i.e. a non-polar solvent that is also a high-boiling point solvent). In some embodiments, the solvent used in the methods described herein may be a non-polar, low-carbon dioxide absorption solvent; or a low-carbon dioxide absorption, high-boiling point solvent; or a non-polar, low-carbon dioxide absorption, high-boiling point solvent. In some embodiments of the methods described herein, the solvent is characterized as having a boiling point of greater than about 177° C. (350° F.), a solubility in water of less than about 3%, and a $CO_2$ Ostwald coefficient of less than about 1.25 at 54° C. (130° F.). In some of these embodiments, the solvent has an average molecular weight from about 125 to about 225. In other embodiments of the methods described herein, the solvent is characterized as having a boiling point of greater than about 191 C (375° F.), a solubility in water of less than about 1%, and a $CO_2$ Ostwald coefficient of less than about 1.1 at 54° C. (130° F.). In some of these embodiments, the solvent has an average molecular weight from about 140 to about 200.

In some embodiments of the methods described herein, the solvent is a selected from a terpene, a paraffin, a monoaromatic hydrocarbon, a polyaromatic hydrocarbon, or a mixture thereof. In some embodiments, the solvent is a paraffin (e.g., a C10-C20 paraffin, such as a C12-C14 paraffin) or an isoparaffin as described above. In some embodiments, the solvent is a terpene. In some embodiments, the solvent is a monoaromatic hydrocarbon. In some embodiments, the solvent is a polyaromatic hydrocarbon. In some embodiments, the solvent is an Isopar™ solvent (commercially available from Exxon) or equivalent thereof, such as a solvent substantially similar to any solvent described in Table 1 (e.g., solvent 1, 2, 3, 4, 5, 6, 7, and/or 8). In some embodiments, the solvent has any one or more properties substantially similar to any solvent described in Table 1 (e.g., solvent 1, 2, 3, 4, 5, 6, 7, and/or 8). In some embodiments, the solvent is selected from Isopar™ L (Table 1; solvent 6), Isopar™ H (Table 1; solvent 4) and Isopar™ M (Table 1; solvent 7). In some embodiments, the solvent is Isopar™ L (Table 1; solvent 6). In some embodiments, the solvent is Isopar™ H (Table 1; solvent 4). In some embodiments, the solvent is Isopar™ M (Table 1; solvent 7).

TABLE 1

| | Solvent | | | | | | | |
|---|---|---|---|---|---|---|---|---|
| | 1 | 2 | 3 | 4 | 5 | 6 | 7 | 8 |
| Tradename | Isopar ™ C | Isopar ™ E | Isopar ™ G | Isopar ™ H | Isopar ™ K | Isopar ™ L | Isopar ™ M | Isopar ™ V |
| Kauri-butanol value[1] | 27 | 29 | 27 | 26 | 27 | 27 | 25 | 23 |

TABLE 1-continued

| | Solvent | | | | | | | |
|---|---|---|---|---|---|---|---|---|
| | 1 | 2 | 3 | 4 | 5 | 6 | 7 | 8 |
| Aniline Point (° F.) | 173 | 167 | 181 | 183 | 181 | 185 | 196 | 198 |
| Flash Point (° F.)[2] | 18 | 45 | 106 | 129 | 135 | 147 | 199 | 265 |
| Distillation (° F.)[3] | 208 | 244 | 320 | 352 | 351 | 372 | 433 | 523 |
| Distillation (° F.)[4] | 219 | 279 | 349 | 370 | 387 | 405 | 489 | 594 |
| Specific Gravity (@60° F.)[5] | 0.70 | 0.72 | 0.75 | 0.76 | 0.76 | 0.77 | 0.79 | 0.83 |
| Saturates | 100 | 100 | 100 | 100 | 99.9 | 99.9 | 99.9 | 99.8 |
| Aromatics | <0.01 | <0.01 | <0.01 | <0.01 | <0.01 | <0.01 | <0.05 | <0.5 |
| Acids (ppm) | None | None | None | None | None | None | None | None |
| Chlorides (ppm) | <3 | <2 | <1 | <3 | 2 | <1 | — | 7 |
| Nitrogen (ppm) | — | <2 | <1 | <1 | <1 | <1 | — | — |
| Peroxides (ppm) | 0 | 0 | Trace | <1 | <1 | <1 | <1 | <1 |
| Sulfur (ppm) | 1 | 1 | 1 | 1 | <2 | <2 | <2 | 1 |
| Surface tension (@77° F.; dynes/cm)[6] | 20.3 | 22.1 | 23.8 | 24.1 | 24.2 | 25.1 | 26.4 | 26.9 |
| Interfacial tension (@77° F.) | 48.9 | 48.9 | 51.6 | 51.4 | 50.1 | 49.8 | 52.2 | 44.9 |
| Demulsibility | Excellent | Excellent | Excellent | Excellent | Excellent | Excellent | Excellent | Excellent |

[1]ASTM D1133;
[2]ASTM D56, TTC;
[3]ASTM D86, IBP;
[4]ASTM D86, Dry Point;
[5]ASDM D1250;
[6]ASTM D971

The solvent used in the methods described herein may further comprise a polymerization inhibitor to aid in reducing unwanted polymerization of isoprene. Accordingly, in some embodiments, the solvent further comprises a polymerization inhibitor (e.g., an inhibitor of isoprene polymerization). Suitable inhibitors include, for example, 2,2,6,6-Tetramethylpiperidine 1-oxyl (TEMPO); 4-Hydroxy-2,2,6,6-tetramethylpiperidine 1-oxyl (TEMPOL); Bis(1-oxyl-2,2,6,6-tetramethylpiperidine-4-yl)sebacate (bridged TEMPO); and t-butyl catechol. In some embodiments of the methods described herein, the solvent comprises a suitable amount of a polymerization inhibitor to sufficiently prevent polymerization of isoprene (e.g., to prevent more than 95%, or more than 97%, or more than 98%, or more than 99%, or more than 99.5% of the isoprene from polymerizing compared to absence of the inhibitor). In some embodiments, the solvent comprises a polymerization inhibitor at a concentration from about 0.001% to about 0.1%, or from about 0.005% to about 0.075%, or from about 0.01% to about 0.05% (w/w) relative to isoprene. In some embodiments, the solvent comprises a polymerization inhibitor at a concentration from about 0.001% to about 0.1%, or from about 0.005% to about 0.075%, or from about 0.01% to about 0.05% (w/w) relative to solvent.

Removal of Volatile Gases

In some aspects, the methods described herein include removing volatile gases from a fermentor off-gas. In some of the embodiments described herein, the fermentor off-gas is contacted with a solvent in a column. In some of these embodiments, the fermentor off-gas is contacted with a solvent in a column to form: an isoprene-rich solution comprising the solvent and a major portion of the isoprene; and a vapor comprising a major portion of the volatile impurity. A stripping vapor flow may be introduced in to the column (e.g., the first column) below the fermentor off-gas feed point, which may aid in separation of the volatile impurity from the remaining solution. The stripping vapor may be introduced by any suitable means (e.g., steam or the column bottom reboiler). In some embodiments, the temperature of the column bottom stream (e.g., at the first column) is much greater than the temperature of the solvent prior to entering the column. In some embodiments, the temperature of the column bottom stream (e.g., at the first column) is greater by any of about 38° C. (100° F.), 52° C. (125° F.), 66° C. (150° F.), 79° C. (175° F.), 93° C. (200° F.), 109° C. (225° F.), 121° C. (250° F.), 135° C. (275° F.), or 149° C. (300° F.). In some embodiments, the temperature of the solvent in the column bottom stream (e.g., at the first column) is from about 66° C. (150° F.) to about 177° C. (350° F.), or about 79° C. (175° F.) to about 149° C. (300° F.), or about 93° C. (200° F.) to about 135° C. (275° F.), or about 110° C. (230° F.) to about 121° C. (250° F.), or about 113° C. (235° F.) to about 118° C. (245° F.). Steam may be directed through the column (at any suitable location, such as near entry of the off-gas and/or the opposite end of the volatile impurity exit) to provide a sweeping vapor phase which may aid in the removal of the volatile impurity. In some embodiments, steam is directed through the column (e.g., through the first column).

Removal of Bio-Byproduct Impurity

In some of the embodiments described herein, the solution comprising isoprene and bio-byproduct impurities (e.g., any isoprene-rich solution transferred from a first column) is transferred to a column (e.g., a second column) wherein isoprene is stripped from the solution. In some of these embodiments, the stripping results in: an isoprene-lean solution comprising a major portion of the bio-byproduct impurity; and a purified isopene composition. In some embodiments, the second column is separated from the first column. In some embodiments, the first and second columns are combined into one column (e.g., the functions of the first and second columns are combined into one column, such as a united tandem column wherein the solvent enters the first column at or near one end and exits the second column at or near an opposite end).

In some embodiments, the temperature of the solution in the column (e.g., at the second column) is from about 66° C. (150° F.) to about 177° C. (350° F.), or about 79° C. (175° F.) to about 149° C. (300° F.), or about 93° C. (200° F.) to about 135° C. (275° F.), or about 110° C. (230° F.) to about 121° C. (250° F.), or about 113° C. (235° F.) to about 118° C. (245° F.). Steam may be directed through the column (at any suitable location, such as the opposite end of the entry point of the isoprene-rich solution and/or the near the isoprene-lean solution exit) to provide a sweeping vapor phase which may aid in recovery of the isoprene from the solvent. In some embodiments, steam is directed through the column (e.g., through the second column).

In some embodiments, stripping the isoprene comprises increasing the pressure of the solution at the column (e.g., the second column). In some of these embodiments, the solution comprising isoprene and bio-byproduct impurity (e.g., any isoprene-rich solution transferred from a first column) at the column (e.g., the second column), has a pressure of more than any of about 5 PSIA, 10 PSIA, 20 PSIA, 30 PSIA, 40 PSIA, 50 PSIA, 60 PSIA, 70 PSIA, 80 PSIA, 90 PSIA, 100 PSIA, 110 PSIA, 120 PSIA, 130 PSIA, 140 PSIA, or 150 PSIA. In some embodiments, the pressure is any of about 5 PSIA to about 150 PSIA, about 5 PSIA to about 100 PSIA, about 10 PSIA to about 75 PSIA, about 10 PSIA to about 65 PSIA, about 10 PSIA to about 60 PSIA, about 15 PSIA to about 50 PSIA, about 15 PSIA to about 45 PSIA, about 15 PSIA to about 35 PSIA, or about 15 PSIA to about 30 PSIA.

Additional Purification

The purified isoprene composition resulting from any of the methods described herein (e.g., a purified isopene composition stripped from the second column) may be further purified by any suitable means for instance as shown in FIG. 1 with reference to adsorption system 36. For example, the purified isoprene composition may be further purified using standard techniques, such fractionation, additional gas stripping, adsorption/desorption, pervaporation, thermal or vacuum desorption of isoprene from a solid phase, countercurrent liquid-liquid extraction with a suitable solvent, or extraction of isoprene immobilized or absorbed to a solid phase with a solvent (see, for example, U.S. Pat. No. 4,703, 007 and U.S. Pat. No. 4,570,029, which are each hereby incorporated by reference in their entireties, particularly with respect to isoprene recovery and purification methods). Suitable solvents include but are not limited to sodium hydroxide, sodium bicarbonate, sodium carbonate, potassium hydroxide, potassium bicarbonate, potassium carbonate, water, ionic liquids such as 1-ethyl-3-methylimidazolium acetate, 1-ethyl-3-methylimidazolium ethyl sulfate, choline acetate, 1-butyl-4-methylpyridinium tetrafluoroborate, 1-hexyl-3-methylimidazolium chloride, 1-ethyl-3-methylimidazolium thiocyanate, and 1-ethyl-3-methylimidazolium hydrogen sulfate.

Additional gas stripping involves the removal of isoprene vapor in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene. The additional purification of the purified isoprene composition may involve one step or multiple steps.

In some embodiments, the resulting isoprene of any of the methods described herein is further purified by treatment with an adsorption system (e.g., an adsorption system comprising activated carbon, alumina, silica, and/or Selexsorb®.) Other suitable materials are zeolites and molecular sieves, see U.S. Pat. Nos. 4,147,848; 5,035,794; and 6,987,152. Suitable filter housings for such a system include those used in the petrochemical industry for removal of impurities present in crude hydrocarbon streams. Examples include those supplied by The Hilliard Corporation (Elmira, N.Y.) and ISC Corporation (Plano, Tex.) In some embodiments, the resulting isoprene of any of the methods described herein is further purified by treatment with an adsorption system comprising silica. In some embodiments, the resulting isoprene of any of the methods described herein is further purified by distillation (e.g., reflux condensation) before or after any other optional added purification. In some embodiments, the resulting isoprene of any of the methods described herein is further purified by treatment with an adsorption system and distillation (e.g., an adsorption system comprising silica and reflux condensation). Adsorption is typically conducted in a packed column configuration and is applicable to isoprene both in vapor or liquid state. If isoprene is fed as a vapor, it is commonly done by feeding it to the top of the column; on the other hand, if it is fed as a liquid, it is usually done by feeding to the bottom. Appropriate adsorbents include but are not limited to the following: activated carbon (e.g., NUCON G60, GC60, Vapor Filtration GC 4×8S, TIGG 5CC 0408), activated alumina (e.g., Axens SAS 351, SAS 830, BASF Selexsorb CD), silica gel (Eagle Chemical Grade 148, Grade 140), and 3A, 5A, or 13× molecular sieves.

Solvent Recirculation and Purification

In any of the methods described herein, the resulting solution following isoprene stripping from the second column (e.g., the isoprene-lean solution comprising a major portion of the bio-byproduct impurity) may be recycled back to the first column for reuse. In some embodiments, bio-byproduct is removed from the recycled solution prior to reuse (e.g., prior to reentering the first column). In some embodiments of any of any method described herein, the method further comprises purifying the isoprene-lean solution to remove a major portion of the bio-byproduct impurity; and transferring the resulting solvent to the first column for reuse. In some embodiments, purifying the stripped solution prior to reuse comprises treating the solution with an adsorption system (e.g., an adsorption system comprising activated carbon, alumina, silica, and/or Selexsorb®.) This absorption may also be done using, e.g., a packed column. In some embodiments, purifying the stripped solution prior to reuse comprises treating the solution with a silica-based adsorption system. In some embodiments, purifying the stripped solution prior to reuse comprises liquid-liquid extraction. In some embodiments, purifying the stripped solution prior to reuse comprises treating the solution comprises distillation. In some embodiments, purifying the stripped solution prior to reuse comprises treating the solution with an adsorption system (e.g., a silica-based adsorption system) and liquid-liquid extraction (in any order). In some embodiments, purifying the stripped solution prior to reuse comprises treating the solution with an adsorption system (e.g., a silica-based adsorption system), liquid-liquid extraction, and distillation (in any order). In any of these embodiments, the stripped solution (e.g., the isoprene-lean solution) may be purified by any of the described means (e.g., adsorption, liquid-liquid extraction, and/or distillation) such that the amount of bio-byproduct in the stripped solution is reduced by more than any of about 5%, 10%, 15%, 20%, 30%, 40%, 50%, 60%, 70%, 80%, 90%, or 95% following purification. In some embodiments, the temperature of the stripped solution (e.g., the isoprene-lean solution comprising a major portion of the bio-byproduct impurity) is reduced prior to reuse in the first column. In some embodiments, the stripped solution is purified and the temperature is reduced prior to reuse in the first column. In some of these embodiments, the temperature is reduced prior to purification. In some of these embodiments, the temperature is reduced after purification. In some embodiments, the temperature of the stripped solution is reduced to less than any of about 95%, 90%, 80%, 70%, 60%, 50%, 40%, 30%, 20%, or 10% of the temperature in ° F. from the second column prior to reuse (e.g., prior to reentering the first column). In some embodiments, the temperature stripped solution is reduced to less than any of about 121° C. (250° F.), 107° C. (225° F.), 93° C. (200° F.), 79° C. (175° F.), 66° C. (150° F.), 52° C. (125° F.), 38° C. (100° F.), 24° C. (75° F.), 10° C. (50° F.) or −4° C. (25° F.). In some embodiments, the temperature stripped solution is reduced to any of about −4° C. (25° F.) to about 121° C. (250° F.), about −4° C. (25° F.) to about 79° C. (175° F.), about −4° C. (25° F.) to about 66° C. (150° F.), about −4° C. (25° F.) to about 38° C. (100° F.), or about −4° C. (25° F.) to about 24° C. (75° F.).

Recollection of Residual Isoprene from Vapor

In some instances, vapor removed from the first column (e.g., the vapor comprising a major portion of the volatile impurity) may also comprise desirable minor amounts of isoprene (e.g., residual isoprene not remaining in the isoprene-rich solution). In some of the embodiments described herein, the vapor comprising a major portion of the volatile impurity additionally comprises a minor portion of isoprene. In any of the embodiments of the methods described herein, the method further comprises removing from vapor a minor portion of the isoprene, if present. The residual isoprene may be recollected for use from the vapor comprising a major portion of the volatile impurity by any suitable means (e.g., with an adsorption system). As described herein for further purification of a purified isopene composition, any suitable technique, such as fractionation, additional gas stripping, adsorption/desorption, pervaporation, thermal or vacuum desorption of isoprene from a solid phase, or extraction of isoprene immobilized or absorbed to a solid phase with a solvent (see, for example, U.S. Pat. No. 4,703,007 and U.S. Pat. No. 4,570,029, which are each hereby incorporated by reference in their entireties, particularly with respect to isoprene recovery and purification methods) may be used to isolate residual isoprene from the vapor phase. As described, isoprene vapor can be removed in a continuous manner, such as, but not limited to, adsorption to a solid phase, partition into a liquid phase, or direct condensation. The removal/purification of isoprene from the vapor phase may involve one step or multiple steps. In any of the embodiments of the methods described herein, the method further comprises removing isoprene (if present) from the vapor, with an adsorption system (e.g., an adsorption system comprises activated carbon, alumina, silica, and/or Selexsorb®). In any of the embodiments of the methods described herein, the method further comprises removing isoprene (if present) from the vapor with an activated carbon adsorption system.

Capture Device

The methods described herein may optionally use a capture device (such as system 38 in FIG. 1) capable of reducing the total amount of undesirable components released into the atmosphere (e.g., $CO_2$) from the vapor. A generic carbon-based adsorption unit such as those used for solvent recovery and supplied by manufacturers including AMCEC Inc. (Lisle, Ill.) and Nucon International Inc. (Columbus, Ohio) would be suitable.

It is often desirable to capture the trace amount of isoprene or other components in the fermentation off-gas that is not recovered by the primary process both for value of the product as well as minimizing release of undesirable components such as carbon dioxide to environment. Trace levels of isoprene and high molecular weight organic compounds can be effectively captured by adsorption on solid surface such as activated carbon (e.g., see NUCON G60, GC60, Vapor Filtration GC 4×85, TIGG 5CC 0408). Carbon dioxide capturing is commonly carried out in a counter-current gas scrubber/absorber where the scrubbing fluid is fed to the top of the liquid contactor while the gas being scrubbed is fed to the bottom. The liquid contactor will have sufficient contact surface or equilibrium stages to achieve the desired reduction in concentration. Common scrubbing fluids include but are not limited to monoethanolamine (MEA), piperazine, water or a combination of all (see, e.g., $CO_2$ Absorption Rate and Solubility in Monoethanolamine/piperazine/Water, Hongyi Dang, et al., *Prepared for presentation at the First National Conference on Carbon Sequestration*, Washington, D.C., May 14-17, 2001).

Resulting Compositions

In some aspects, the methods described herein provide a purified isoprene composition, wherein a purified isoprene composition is an isoprene composition that has been separated from at least a portion of one or more components that are present in the fermentor off-gas. In some embodiments, the purified isoprene composition has a purity of greater than about 75% (w/w). In some embodiments, the purified isoprene composition has a purity of greater than any of about 80%, 85%, 90%, 95%, 97%, 98%, 99%, 99.5%, 99.5%, or 99.95% (w/w).

In any of the embodiments described herein, the purified isoprene composition comprises no more than about 20% (w/w) bio-byproduct impurity. In some embodiments, the purified isoprene composition comprises less than about 15%, 12%, 10%, 8%, 6%, 5%, 4%, 3%, 2%, 1%, 0.075%, 0.5%, 0.25%, 0.1%, 0.05%, 0.02%, 0.01%, or 0.005% (w/w) bio-byproduct impurity relative to the weight of the isoprene. In some embodiments, the purified isoprene composition comprises less than about 50% (w/w) bio-byproduct impurity relative to the bio-byproduct impurity of the fermentor off-gas. In some embodiments, the purified isoprene composition comprises less than any of about 40%, 35%, 30%, 25%, 20%, 15%, 10%, 7.5%, 5%, 2.5%, 1%, or 0.5% (w/w) bio-byproduct impurity relative to the bio-byproduct impurity of the fermentor off-gas.

In any of the embodiments described herein, the purified isoprene composition comprises no more than about 20% (w/w) volatile impurity. In some embodiments, the purified isoprene composition comprises less than about 15%, 12%, 10%, 8%, 6%, 5%, 4%, 3%, 2%, 1%, 0.075%, 0.5%, 0.25%, 0.1%, or 0.05% (w/w) volatile impurity. In some embodiments, the purified isoprene composition comprises less than about 50% (w/w) volatile impurity relative to the volatile impurity of the fermentor off-gas. In some embodiments, the purified isoprene composition comprises less than any of about 40%, 35%, 30%, 25%, 20%, 15%, 10%, 7.5%, 5%, 2.5%, 1%, or 0.5% (w/w) volatile impurity relative to the volatile impurity of the fermentor off-gas.

In any of the embodiments described herein, the purified isoprene composition comprises no more than about 20% (w/w) of a one or more compounds selected from $H_2O$, $CO_2$, CO, $N_2$, $CH_4$, $H_2$ and $O_2$. In some embodiments, the purified isoprene composition comprises no more than about 15%, 12%, 10%, 8%, 6%, 5%, 4%, 3%, 2%, 1%, 0.075%, 0.5%, 0.25%, 0.1%, or 0.05% (w/w) of one or more compounds selected from $H_2O$, $CO_2$, CO, $N_2$, $CH_4$, $H_2$ and $O_2$. In some embodiments, the purified isoprene composition comprises less than about 50% (w/w) of one or more compounds selected from $H_2O$, $CO_2$, CO, $N_2$, $CH_4$, $H_2$ and $O_2$ relative to the fermentor off-gas. In some embodiments, the purified isoprene composition comprises less than any of about 40%, 35%, 30%, 25%, 20%, 15%, 10%, 7.5%, 5%, 2.5%, 1%, or 0.5% (w/w) one or more compounds selected from $H_2O$, $CO_2$, CO, $N_2$, $CH_4$, $H_2$ and $O_2$ relative to the fermentor off-gas.

In any of the embodiments described herein, the purified isoprene composition comprises no more than about 20% (w/w) $CO_2$. In some embodiments, the purified isoprene composition comprises no more than about 15%, 12%, 10%, 8%, 6%, 5%, 4%, 3%, 2%, 1%, 0.075%, 0.5%, 0.25%, 0.1%, or 0.05% (w/w) $CO_2$. In some embodiments, the purified isoprene composition comprises less than about 50% (w/w) $CO_2$ relative to the amount of $CO_2$ of the fermentor off-gas. In some embodiments, the purified isoprene composition comprises less than any of about 40%, 35%, 30%, 25%, 20%, 15%, 10%, 7.5%, 5%, 2.5%, 1%, or 0.5% (w/w) $CO_2$ relative to the amount of $CO_2$ of the fermentor off-gas.

In any of the embodiments described herein, the purified isoprene composition comprises no more than about 20% (w/w) $O_2$. In some embodiments, the purified isoprene composition comprises no more than about 15%, 12%, 10%, 8%, 6%, 5%, 4%, 3%, 2%, 1%, 0.075%, 0.5%, 0.25%, 0.1%, or 0.05% (w/w) $O_2$. In some embodiments, the purified isoprene composition comprises less than about 50% (w/w) $O_2$ relative to the amount of $O_2$ of the fermentor off-gas. In some embodiments, the purified isoprene composition comprises less than any of about 40%, 35%, 30%, 25%, 20%, 15%, 10%, 7.5%, 5%, 2.5%, 1%, or 0.5% (w/w) $O_2$ relative to the amount of $O_2$ of the fermentor off-gas.

Isoprene Compositions

Also provided are purified isoprene compositions (e.g., compositions comprising purified bioisoprene). In some embodiments is provided a purified isopene composition preparable by any of the methods described herein. In some embodiments, is provided a purified isoprene composition prepared by any of the methods described here.

In some embodiments, there is provided a composition of isoprene (e.g., bioisoprene) comprising less than about 15%, 12%, 10%, 8%, 6%, 5%, 4%, 3%, 2%, 1%, 0.075%, 0.5%, 0.25%, 0.1%, 0.05%, 0.02%, 0.01%, or 0.005% (w/w) bio-byproduct impurity relative to the weight of the isoprene. In some embodiments, is provided a composition of isoprene (e.g., bioisoprene) comprising less than about 15%, 12%, 10%, 8%, 6%, 5%, 4%, 3%, 2%, 1%, 0.075%, 0.5%, 0.25%, 0.1%, or 0.05% (w/w) volatile impurity. In some embodiments, is provided a composition of isoprene (e.g., bioisoprene) comprising less than about 15%, 12%, 10%, 8%, 6%, 5%, 4%, 3%, 2%, 1%, 0.075%, 0.5%, 0.25%, 0.1%, 0.05%, 0.02%, 0.01%, or 0.005% (w/w) bio-byproduct impurity relative to the weight of the isoprene and less than about 15%, 12%, 10%, 8%, 6%, 5%, 4%, 3%, 2%, 1%, 0.075%, 0.5%, 0.25%, 0.1%, or 0.05% (w/w) volatile impurity relative to the weight of the composition. In any of these embodiments, the isoprene composition comprises greater than any of about 80%, 85%, 90%, 95%, 97%, 98%, 99%, 99.5%, 99.5%, or 99.95% (w/w) isoprene relative to the weight of the composition. In any of these embodiments, the isoprene composition comprises greater than about 99.94%, 99.94%, 99.95%, 99.96%, 99.97%, 99.98%, or 99.99% isoprene (w/w) relative to the weight of all C5 hydrocarbons. In any of these compositions, the bio-byproduct impurity comprises one or more compounds selected from the group consisting of 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-but-1-enyl acetate, 3-methyl-2-but-1-enyl acetate, (E)-3,7-dimethyl-1,3,6-octatriene, (Z)-3,7-dimethyl-1,3,6-octatriene, and 2,3-cycloheptenolpyridine or as indicated above.

In some embodiments, is provided a composition of isoprene (e.g., bioisoprene) comprising less than about 5% (or 1%, or 0.5%, or 0.05%, or 0.005%) (w/w) bio-byproduct impurity relative to the weight of the isoprene; less than about 10% (or 1%, or 0.1%, or 0.05%) (w/w) volatile impurity relative to the weight of the composition; and greater than about 95% (or 98%, or 99%, or 99.95%) (w/w) isoprene relative to the weight of the composition, wherein the isoprene composition comprises greater than about 99.9% (or 99.95%, or 99.97%, or 99.99%) isoprene (w/w) relative to the weight of all C5 hydrocarbons. In some embodiments, is provided a composition of isoprene comprising less than about 1% (w/w) bio-byproduct impurity relative to the weight of the isoprene; less than about 5% (w/w) volatile impurity relative to the weight of the composition; and greater than about 98% (w/w) isoprene relative to the weight of the composition, wherein the isoprene composition comprises greater than about 99.95% isoprene (w/w) relative to the weight of all C5 hydrocarbons. In some embodiments, is provided a composition of isoprene comprising less than about 1% (w/w) bio-byproduct impurity relative to the weight of the isoprene; less than about 5% (or 2%, or 1%, or 0.5%) $CO_2$ (w/w) relative to the weight of the composition; and greater than about 98% (w/w) isoprene relative to the weight of the composition, wherein the isoprene composition comprises greater than about 99.95% isoprene (w/w) relative to the weight of all C5 hydrocarbons.

In some embodiments of any of the compositions, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon.

In any of the compositions described herein, the composition may comprise greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

Additional methods and compositions are described in as described in International Patent Application Publication No. WO2009/076676; U.S. patent application Ser. Nos. 12/496,573, 12/560,390, 12/560,317, 12/560,370, 12/560,305, and 12/560,366; and U.S. provisional patent application Nos. 61/187,930, 61/187,934, and 61/187,959, all of which are incorporated by reference in their entireties, particularly with respect to compositions and methods for producing isoprene.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES

Example 1 is recovery of isoprene from fermentation off-gas by absorption and stripping, including:

(1) Absorption of isoprene from fermentation off-gas. Fermentation off-gas comprising isoprene, bio-byproduct impurities and volatile impurities is introduced into a glass gas scrubber unit (Part # CG-1830-10, supplied by ChemGlass, Vineland, N.J., USA) at a flow rate of 4 L/min. The reservoir of the scrubber contains 0.5 L of Isopar® M (ExxonMobil, Tex.) which is recirculated at a rate of 2 L/min. The solvent is recirculated until equilibrium with the fermentation off-gas is achieved, as determined by GC/MS analysis of the fermentation off-gas prior to entering the gas scrubber unit, the isoprene-rich Isopar solvent and the tail-gas emerging from the gas scrubber unit. Equilibrium occurs at the point where the isoprene concentration in the feed gas is the same as that in the tail gas emerging from the scrubber. Another indication is the point at which the isoprene-concentration in the solvent attains a steady state.

(2) Stripping and condensation of isoprene. Stripping of isoprene from the isoprene-rich Isopar solvent is achieved by reconfiguring the gas scrubber unit, whereby steam is added to the gas scrubber unit in place of the fermentation off-gas feed at a rate of 4 L/min. The solvent is recirculated at a rate of 2 L/min and the isoprene vapor stripped from the solvent emerges from the top of the gas scrubber unit, along with amounts of bio-byproduct impurities.

The isoprene vapor emerging from the gas scrubber unit is then condensed using a Graham condenser or similar glass condenser cooled with a coolant at 0 to 10° C. The isoprene condensate is collected and inhibited through the addition of 150 ppm t-butylcatechol. The purity of the liquid isoprene is determined by GC/MS according to procedures known to those familiar in the art.

The following describes two exemplary sets of columns for use here, suitable for large scale (manufacturing) or smaller scale (a pilot plant or test apparatus) processes as determined by simulation.

Example A below uses tray columns, there being thirteen trays for the absorber column 14 and sixteen trays for the stripper column 24. Example B below uses structured packing columns, there being ten stages (tray equivalents) for the absorber column 14 and eleven stages for the stripper column 24. The goal is 99.9% recovery of the isoprene. All these parameters and these examples are merely illustrative.

|  | Solvent gpm/MSCFH gas feed | % Recovery of Contained Isoprene |
|---|---|---|
| Example A |  |  |
| Fermentor Gas | 0.38 | 89.0% |
| Isoprene | 0.40 | 91.0% |
| Concentration: | 0.41 | 94.0% |
| 0.12 mole fraction | 0.43 | 97.5% |
| 0.21 wt. fraction | 0.47 | 99.9% |
| Lbs. Stripping Steam/Lb. Recovered Isoprene @ 99.9% Recovery |  | 1.10 |
| Recovered Isoprene Purity |  | 99.8 Wt % |
| Example B |  |  |
| Fermentor Gas | 0.28 | 89.0% |
| Isoprene | 0.29 | 91.0% |
| Concentration: | 0.31 | 94.0% |
| 0.04 mole fraction | 0.33 | 97.5% |
| 0.08 wt. fraction | 0.41 | 99.9% |
| Lbs. Stripping Steam/Lb. Recovered Isoprene @ 99.9% Recovery |  | 2.79 |
| Recovered Isoprene Purity |  | 99.8 Wt % |

Example 2 is of recovery of isoprene from fermentation off-gas using solvent, by a laboratory scale gas scrubber unit as described above.

Fermentation off-gas including isoprene, bio-byproduct impurities and volatile impurities was introduced into a laboratory-type glass gas scrubber unit including an absorption column (Part # CG-1830-10, supplied by ChemGlass, Vineland, N.J., USA), at a flow rate of 8 L/min. The isoprene concentration was in the range of 1.8 to 2.1% v/v as determined by online mass spectrometry using a Hiden HPR-20 mass spectrometer (supplied by Hiden Analytical, United Kingdom). The reservoir of the scrubber contained 1 L of Isopar®L isoparaffinic solvent as described above, hereinafter "solvent" (supplied by ExxonMobil Chemical Co., Houston, Tex., USA) which was recirculated at a rate of 2 L/min at room temperature (20° C.). The concentration of isoprene in the Isopar solution was about 1% by volume during this process. The process was continued until equilibrium with the fermentation off-gas was achieved, as determined by online mass spectrometer analysis of the fermentation off-gas prior to entering the gas scrubber unit and the tail-gas emerging from the gas scrubber unit. These data were used to calculate the absorption efficiency of isoprene (vertical axis) as a function of time (horizontal axis), as shown in the plot of FIG. 2.

Figure 2:
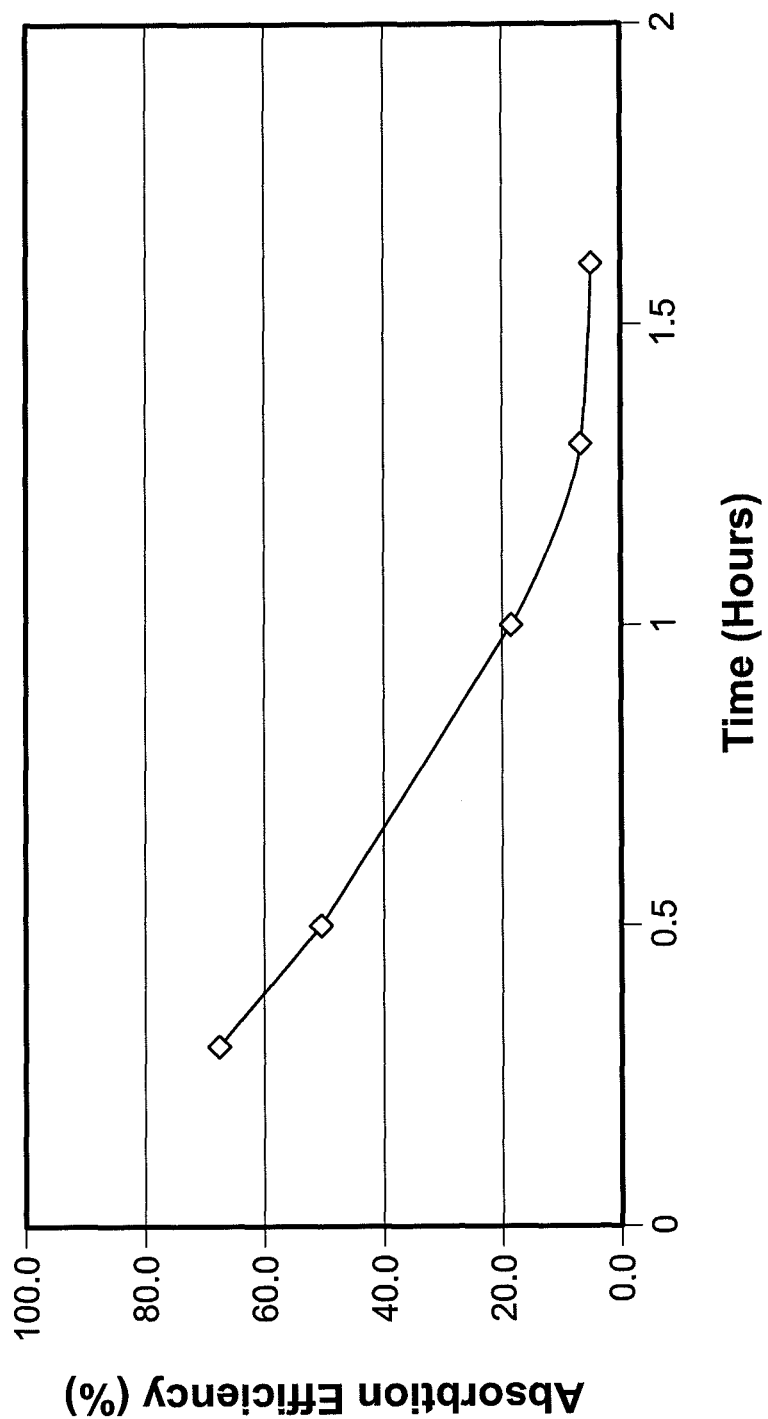
FIG. 2 is a plot of isoprene absorption efficiency.

The cumulative amount of isoprene collected was calculated by multiplying by the total productivity of isoprene by the average absorption efficiency over the duration of the process, as determined by the extrapolated area under the plot of FIG. 2. At an isoprene concentration of 2% v/v and an off-gas flow of 8 L/min, the total amount of isoprene produced by the fermentor over the 1.6 hour period was approximately 40 g, of which around 30% was collected, giving a theoretical concentration in the range of 10 to 12 g/L isoprene in the solvent. Following the completion of the process, the solution was removed from the gas scrubber for subsequent analysis, stripping, and condensation to recover pure isoprene liquid.

Example 3 is of an analysis of isoprene solution.

The isoprene solution generated by the above described gas absorption was analyzed to determine the isoprene content and the identity of major impurities using both headspace and liquid GC/MS (gas chromatography/mass spectrometry) methods. Isoprene concentration was determined using a headspace method, whereby 1 mL of the isoprene solution was placed into a 20 mL head space vial and incubated at 40° C. for 5 minutes prior to a 100 µL headspace injection. The GC/MS method used helium as the carrier gas at 1 mL/min, an inlet temperature of 230° C. and a split ratio of 100:1. A Zebron TM ZB-5 GC column (30 m×0.25 mm×0.25 µm and supplied by Phenomenex, Torrance, Calif., USA) was employed, with the mass spectrometer detector operating in SIM mode monitoring ions at m/z 41, 56, 68, 69, 71 and 86. The heating began at 50° C., held for 2 minutes, followed by an increase to 75° C. at a rate of 20° C./min, then increasing to 250° C. at a rate of 35° C./min. The final temperature of 250° C. was held for 0.75 minutes for a total run time of 9 minutes. Under these conditions, isoprene eluted at 1.68 minutes and solvent L-derived hydrocarbons eluted between 5.5 and 6.5 minutes. The method was calibrated using isoprene/solvent standards ranging in concentration from 1 mg/mL to 20 mg/mL. The concentration of the isoprene/solvent composition generated in Example 2 was determined to be 9.4 g/L using this method.

Figure 3:
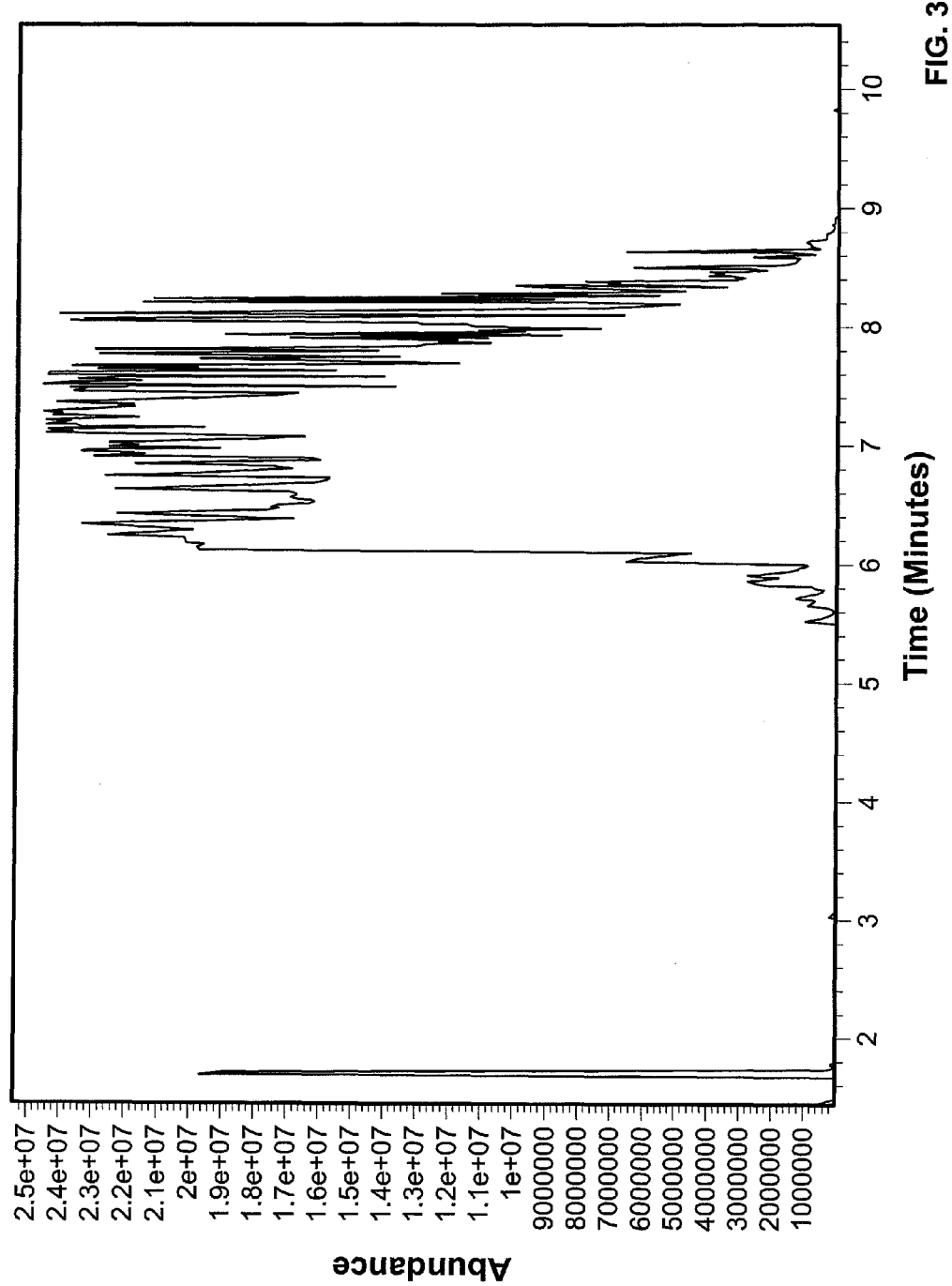
FIG. 3 is an analysis of isoprene/solvent composition.

For identification of bio-byproduct impurities present in the isoprene solution, a liquid GC/MS method was employed whereby a 1 µL sample was injected into a GC inlet held at 250° C. with a 20:1 split utilizing helium as the carrier gas at a flow rate of 1 mL/min. The Zebron ZB-5 GC column (30 m×0.25 mm×0.25 um) was employed, with the mass spectrometer detector operating in scan mode monitoring ions between m/z 29 and 350. The heating began at 50° C., held for 2 minutes, followed by an increase to 320° C. at a rate of 20° C./min with a final hold time of 2.5 minutes for a total run time of 18 minutes. Under these conditions as shown in FIG. 3, isoprene eluted at 1.69 minutes (horizontal axis) and solvent-derived hydrocarbons eluted between 5.5 and 9 minutes. Several bio-byproduct impurities were identified (see Table 2), in addition to low molecular weight saturated hydrocarbons derived from the solvent. Note that some of these impurities themselves are of commercial value and could be further isolated as bio-byproducts using well known methods in an industrial scale version of the present purification process.

TABLE 2

| Compound | Retention time (min) |
|---|---|
| Ethanol | 1.59 |
| Acetone | 2.65 |
| 3-methyl-3-buten-1-ol | 3.02 |
| 3-methyl-2-buten-1-ol | 3.48 |
| 3-methyl-2-buten-1-yl acetate | 4.69 |

Figure 4:
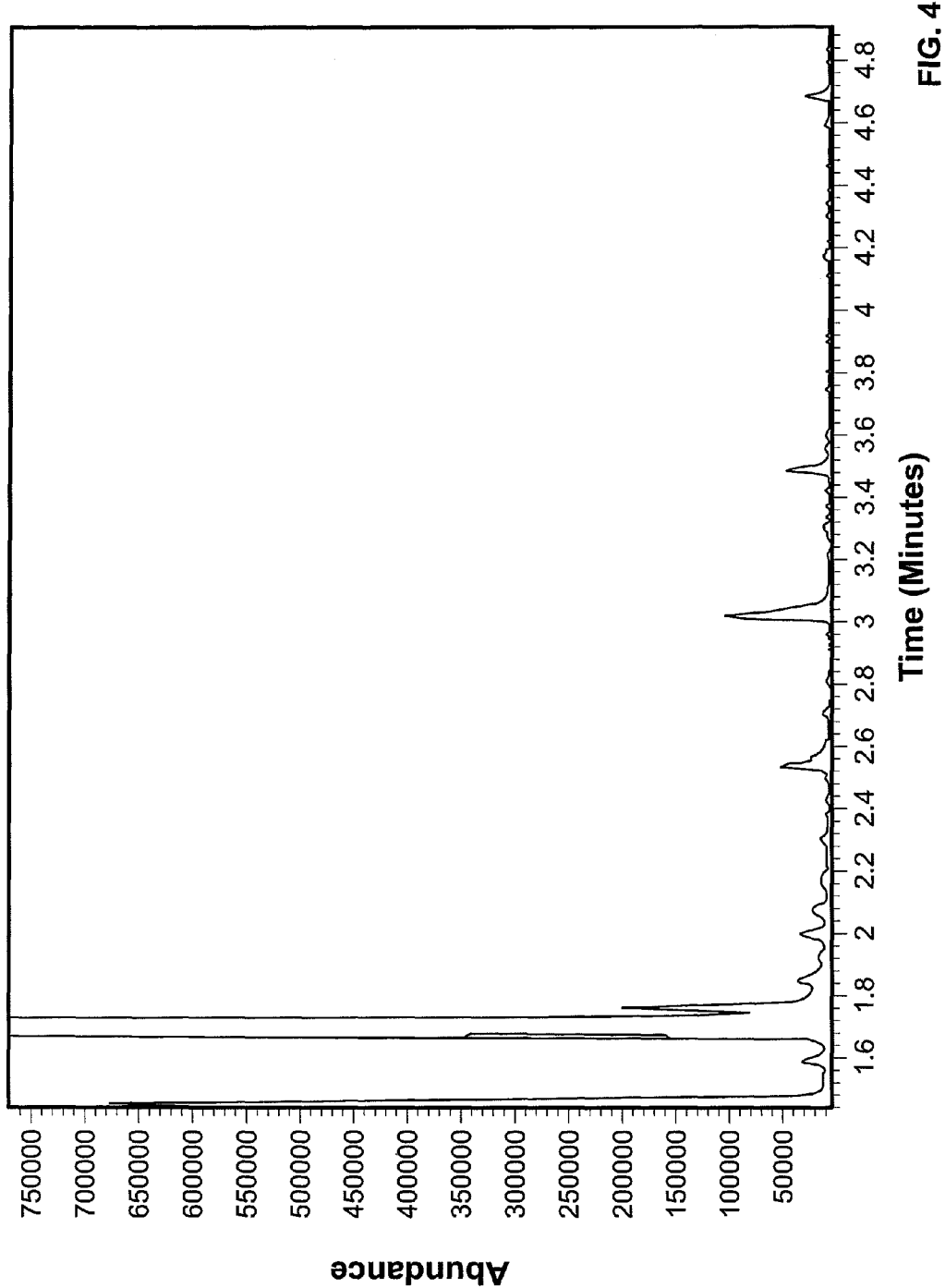
FIG. 4 shows detail of FIG. 3.

FIG. 4 is an expansion of the left hand portion GC/MS spectrum of FIG. 3 from 1.6 minutes to 4.8 minutes (horizontal axis).

Example 4 is of stripping and condensation of isoprene liquid from isoprene/solvent solutions.

Two methods (referred to above) were used to recover isoprene liquid from isoprene/solvent solutions generated as described in Example 2:

(a) In a laboratory scale process, stripping of the isoprene from the solvent was achieved by transferring the isoprene/solvent solution to a 3-necked 1 L round bottom flask fitted with a laboratory-type dry-ice cooled Dewar-style distillation head (Part #CG-1251, supplied by Chemglass, Vineland, N.J., USA), a gas sparge inlet and a stirrer bar. The condenser was fitted with a 50 mL receiving flask for the liquid isoprene product. The outlet from the apparatus was sent to a dry-ice filled cold trap and a bubbler to monitor gas flow. The flask was heated to 80° C. in an oil bath and nitrogen gas bubbled through the solution a rate of less than 1 L/minute. Over the course of 2 hours, liquid isoprene (about 4 mL) was collected in the receiving flask.

(b) The apparatus described in (a) above was modified by coupling a 3-stage Snyder distillation column coupled between the 3-neck flask and the condenser. The temperature of the oil bath was raised to 120° C. In this case, steam was used instead of nitrogen gas, the flow of which was adjusted to maintain a temperature gradient in the distillation column ranging from 100° C. at the bottom to 34° C. at the top. Over the course of 2 hours, liquid isoprene (about 6 mL) was collected in the receiving flask.

Analysis of solvent following this distillation was performed using the headspace GC/MS method described in Example 3 in order to determine the extent to which isoprene was stripped from the solvent. The results are shown in Table 3:

TABLE 3

| Stripping method | Isoprene concentration in solvent (g/L) | | Stripping Efficiency |
|---|---|---|---|
| | Initial | Final | |
| Nitrogen | 8.55 | 5.52 | 41% |
| Steam | 9.38 | 3.84 | 55% |

Example 5 is an analysis of isoprene liquid recovered by absorption/stripping using solvent.

Figure 5:
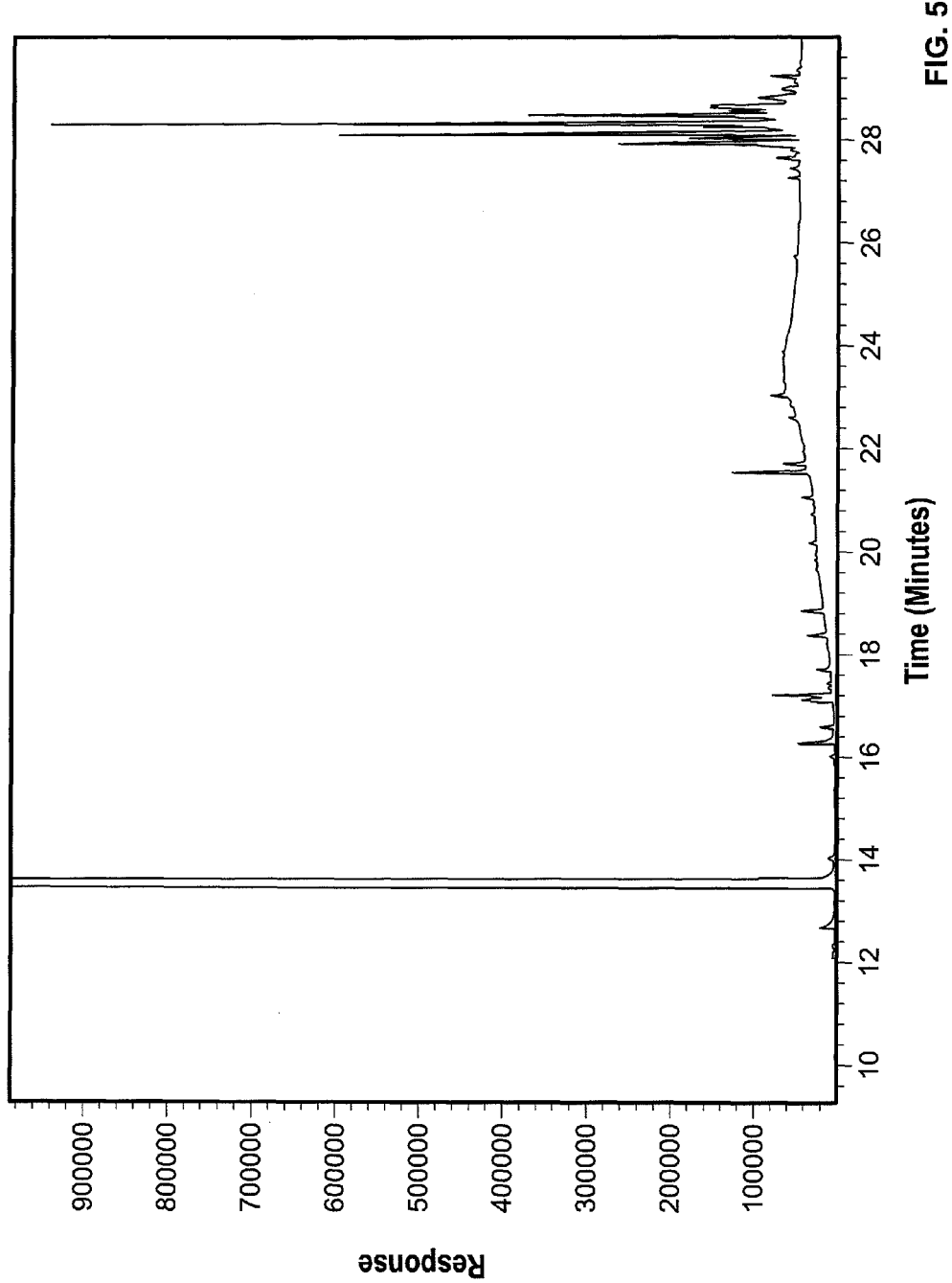
FIG. 5 is a plot of isoprene recovered from a solution.

The isoprene liquid generated as described in Example 4 was analyzed using GC/FID (gas chromatography/flame ionization detector) and GC/MS methods to assess overall purity and to identify both bio-byproduct and other impurities present. The GC/FID analysis was performed using a DB-Petro column (100 m×0.25 mm, 0.50 um film thickness supplied by Agilent Technologies, Santa Clara, Calif., USA) held at 50° C. for 15 minutes. The method utilized helium as the carrier gas at a flow of 1 mL/min. The injection port was held at 200° C. and operated in splitless mode. An Agilent 5793N mass selective detector was fun in full scan mode from m/z 19 to m/z 250. FIG. 5 is a GC/FID plot of isoprene recovered from the solvent in this example. Under these conditions, isoprene was observed to elute at 13.4 min, and bio-byproduct impurities and volatile solvent derived impurities between 12.6 and 23.0 minutes. Solvent hydrocarbons eluted between 27 and 29.5 minutes.

Example 6 is of removal of polar bio-byproduct impurities from the solvent in a final purification process as referred to above.

Polar bio-byproduct impurities present in the isoprene-solvent were removed by passage over an adsorbent as described above, in particular adsorbents based on silica and alumina. For example, the solvent solution (100 mL) obtained following stripping of the isoprene (see Example 4) was pumped through a bed of Selexsorb CDX adsorbent (10 g of Selexsorb CDX from BASF) over 20 minutes and filtered solvent analyzed by GC/FID. The chromatogram (not shown) showed that the majority of bio-byproduct impurities were removed. As an alternative (see below), a silica based adsorbent may be used.

Figure 6:
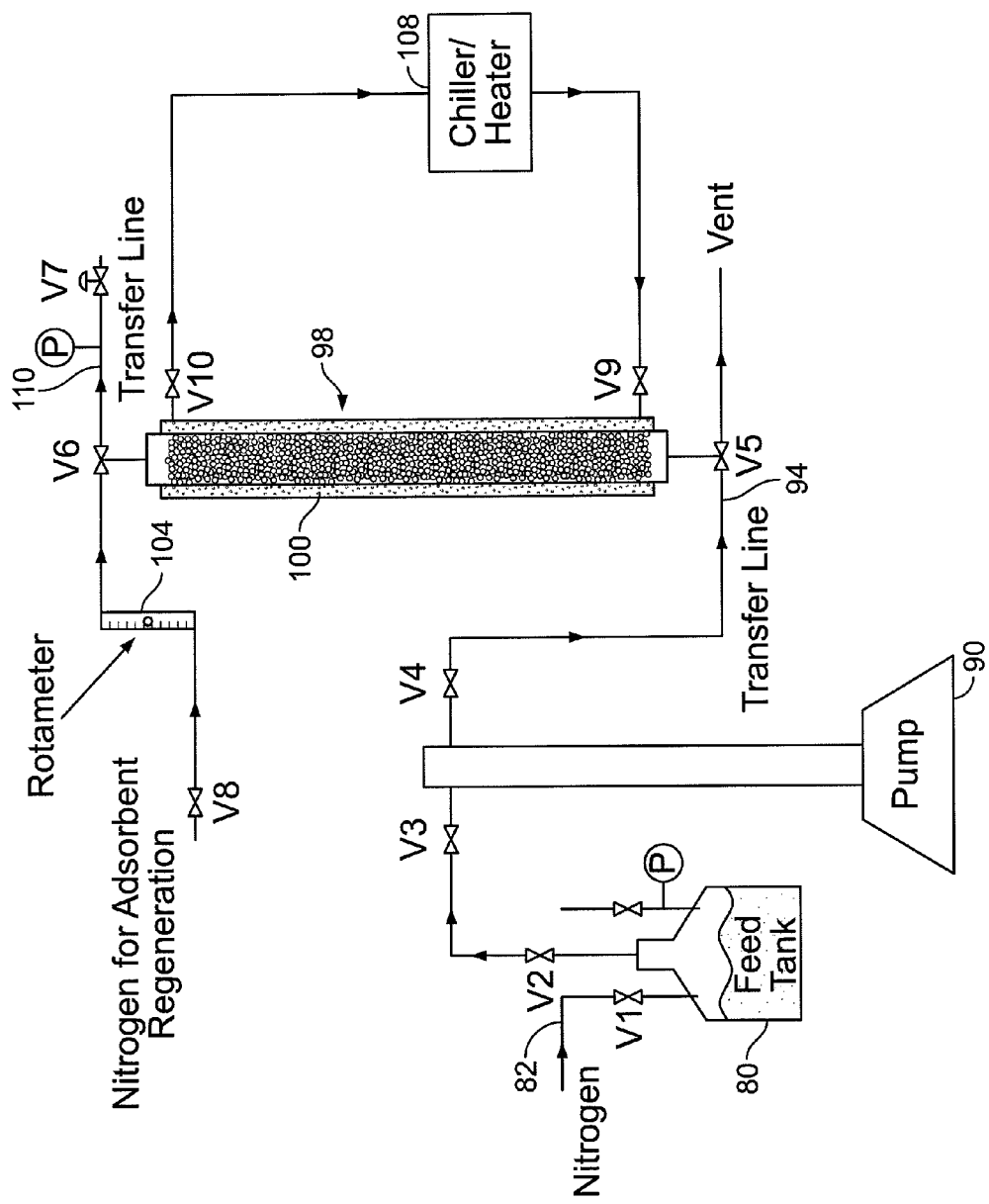
FIG. 6 is a diagram of a process and associated apparatus to further purify isoprene.

FIG. 6 shows an example of an adsorbent process apparatus (such as system 36 in FIG. 1) where the isoprene solution output from the upstream portion of the FIG. 1 apparatus is initially held in feed tank (reservoir) 80. A flow of nitrogen gas is provided via flow line 82 to reservoir 80 to maintain a pressure of about 90 PSI (pounds per square inch, about 6 atmospheres measured at pressure regulator P), via valve V1. Valve V2 admits the pressurized isoprene solution to valves V3, V4 between which is coupled a pump 90. The pumped solution is carried by transfer line 94 via valve V5 to a conventional adsorbing bed 98, which is a bed of alumina, or silica or other adsorbent as described above such as Selexsorb CDX, housed in a conventional jacket 100.

A second flow of nitrogen gas is provided via valves V8 and V6 with intervening rotameter 104 to measure the gas flow rate. This second flow of nitrogen gas is coupled to the bed 98. As is conventional, the nitrogen gas at value V6 and the isoprene solution at valve V5 are supplied alternately to allow flushing via the nitrogen gas of the adsorbent in the bed 98. The flushing removes the impurities in the isoprene solution which have been adsorbed by the bed. This process allows the impurities to be vented with the flushing nitrogen gas via valve V5 during this regeneration of the bed. Valves V9, V10 couple a chiller/heater unit 108 to the bed 98 to keep both the flushing nitrogen gas and the isoprene solution at their proper temperatures. Finally, the resulting purified isoprene solution is output via transfer line 110 (having a second pressure regulator P) and valve V7.

In a laboratory scale example, isoprene derived from a bioisoprene composition (1 mL with 150 ppm TBC added) was treated with one bead (diameter ⅛" which is 3 mm, about 90 mg by weight) of either Selexsorb® CD, or Selexsorb® CDX in a GC vial for 1 hour with occasional agitation. The Selexsorb® products changed color from white to yellowish within 10 minutes. Samples were analyzed by gas chromatography/mass spectrometry and the spectra overlaid to highlight the degree to which impurities were removed. The extent of polar impurity removal was determined and the results shown in Table 3A.

TABLE 3A

| Compound | Selexsorb ® CD | Selexsorb ® CDX |
| --- | --- | --- |
| Ethanol | >90% | >90% |
| Acetone | >90% | >90% |
| Methacrolein | >90% | >90% |
| Ethyl acetate | >90% | >90% |
| 3-Methyl-3-buten-2-ol | >90% | >90% |
| Methylvinyl ketone | >90% | >90% |
| 2-vinyl-2-methyloxirane | >90% | >90% |
| 3-methyl-3-buten-1-ol | 94% | 96% |
| 3-methyl-3-buten-1-yl acetate | 68% | 75% |

Further Isoprene Purification—Liquid Extraction

As explained above and as depicted in FIG. 6, it is desirable to further purify the isoprene solution, which typically contains a number of impurities of various types. In one embodiment, further purification was achieved using the liquid extraction method referred to above, to remove semi-polar impurities.

It has been determined that a significant difference between conventional isoprene derived from petroleum and the present bioisoprene derived from fermentation is the presence in the fermentation-type isoprene of large amounts of biological ("bio") by-products that are polar in nature in terms of their chemistry. These impurities fall into chemical classes including acetates, alcohols, ketones, and acids as described above. These impurities interfere or inhibit the subsequent necessary polymerization of the isoprene as described above and therefore must be removed from the recovered isoprene prior to the downstream polymerization step. The adsorbent process described with reference to FIG. 6 generally would not remove such polar impurities.

It has been found that contacting the bioisoprene with de-ionized (DI) water or a base (alkaline) de-ionized water solution removed a significant amount of such impurities. Multiple contacts with the water or alkaline water solution will reduce impurities to any desirable level. In yet another example, Table 4 shows (left hand column) the various impurities, the proportion of the impurity removed in this example with contact of an equal volume of a alkaline water solution (center column), and (right hand column) the proportion of the impurity removed by contact with an equal volume of deionized water.

TABLE 4

| Impurity (0.1M in n-hexane) | % Removed (contact with equal volume of (10) wt % NaOH) | % Removed (contact with equal volume of DI water) |
| --- | --- | --- |
| 2-Methylfuran | 2.6% | 0.4% |
| Methanol | 100.0% | 100.0% |
| Prenol | 55.7% | 18.3% |
| Acetone | 71.2% | 90.1% |
| Acetic Acid | Co-elute with hexane | |
| Methyl Isobutyrate | 89.3% | 9.1% |
| Methyl Acetate | 38.3% | 24.2% |
| Dimethyl Bisulfide | 4.4% | 2.6% |

Thus it has been found that the base (alkaline) water process in the second column of Table 4 was effective in removing all these impurities to a large extent, except for the 2-methylfuran and the dimethyl disulfide. Only a small proportion of these two impurities was removed. However, it has been found that the 2-methylfuran is not significant in terms of preventing polymerization. Hence dimethyl sulfide is the key remaining impurity. It is well known that dimethyl disulfide is a particularly potent polymerization "poison."

An apparatus to perform this "caustic wash" process is conventional and would include a suitable vessel to hold the caustic solution and into which a volume of the isoprene solution is pumped. The vessel would be equipped with a suitable stirring or mixing device, since the isoprene solution is not miscible with water. Hence the above reference to "contacting" the isoprene solution with the caustic solution long enough to achieve the desired extraction of the impurities into the caustic solution. Then the caustic solution is separated conventionally from the purified isoprene solution. This caustic wash process may be a conventional batch or continuous process. This caustic wash process may be performed upstream or downstream of the FIG. 6 adsorption system. Or, the caustic wash and adsorption may be performed together by, e.g., impregnating the silica or alumina adsorbent with a suitable caustic compound, as is known in the field.

Figure 7:
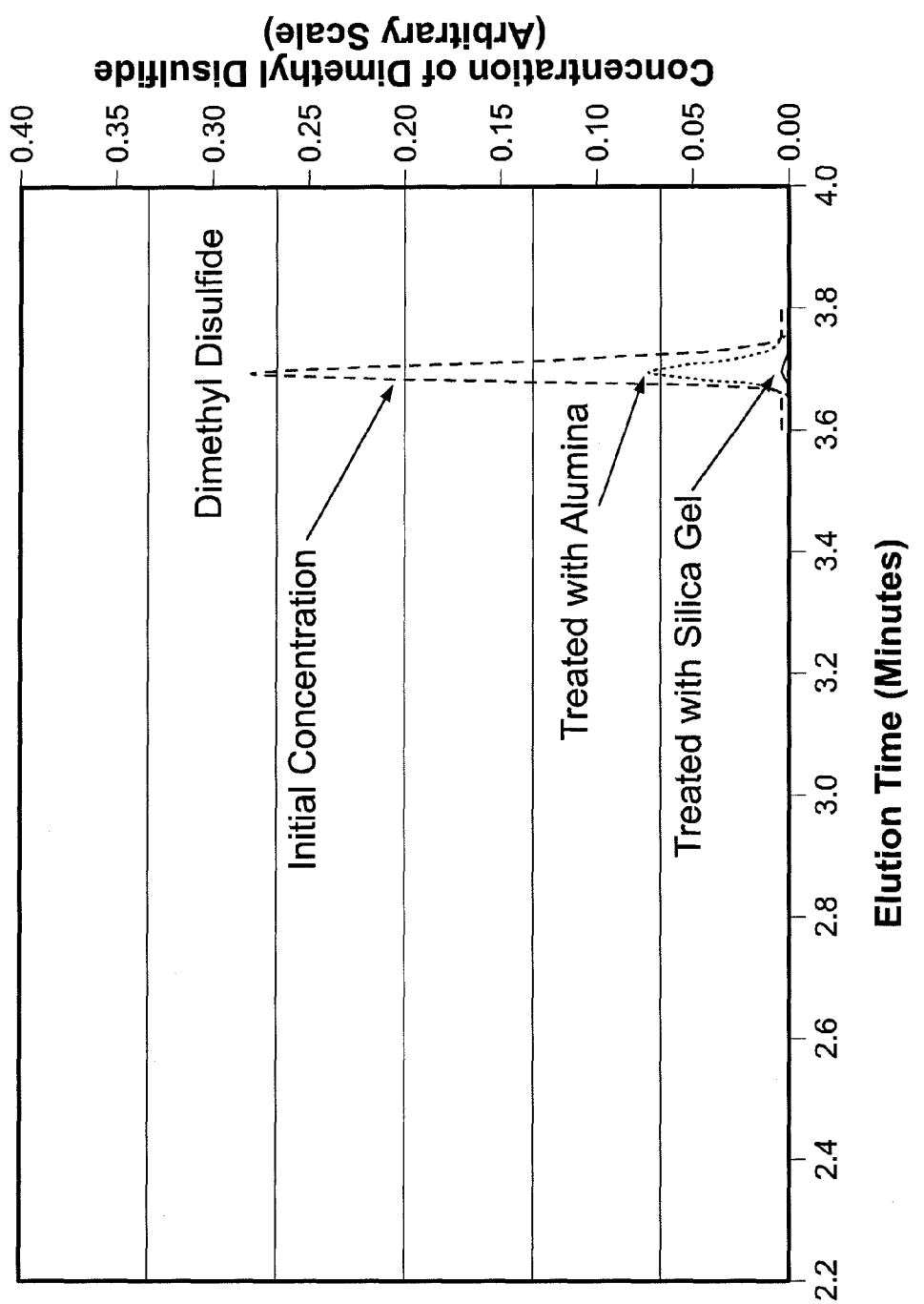
FIG. 7 is a plot of impurities in isoprene.

Further, an effective way of removing the dimethyl disulfide is the adsorption technique as described above with reference to FIG. 6. FIG. 7 is a plot of impurities in bioisoprene over time (horizontal axis) where the right hand peak shows the dimethyl disulfide concentration after an elution time (in a laboratory type adsorbent bed purifying apparatus) indicated along the horizontal axis. As seen, the initial concentration of dimethyl disulfide was quite high then fell substantially when treated with an adsorption system having alumina, and fell even further when treated with the silica adsorption, to be almost imperceptible.

Figure 8:
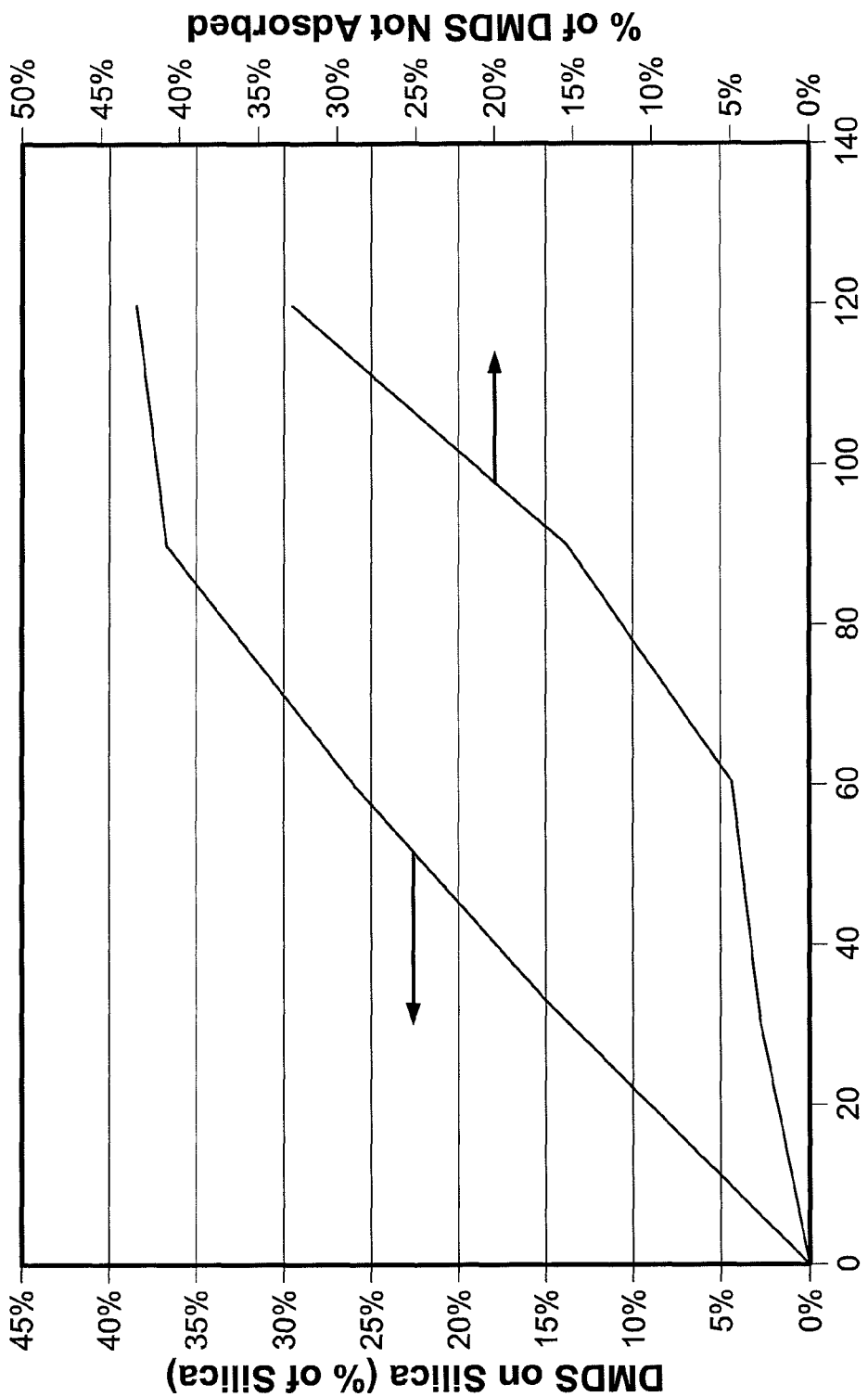
FIG. 8 is a plot of a concentration of the impurity dimethyl disulfide over time.

FIG. 8 also refers to this adsorbent technique and shows time along the horizontal axis, and along the left hand vertical axis and associated left hand plot the proportion of dimethyl disulfide in the silica as a percentage of the silica, and along the right hand vertical axis and associated right hand plot the percentage of dimethyl disulfide in the feed that is not absorbed by the silica over time. Therefore the effectiveness of the adsorption process diminished sharply beginning at about 60 minutes as the adsorbent bed became loaded (saturated) with the dimethyl disulfide. Per the left hand plot, the bed becomes saturated at about 38% dimethyl disulfide. Hence the need to periodically flush (regenerate) the bed as described with reference to FIG. 6.

Figure 9:
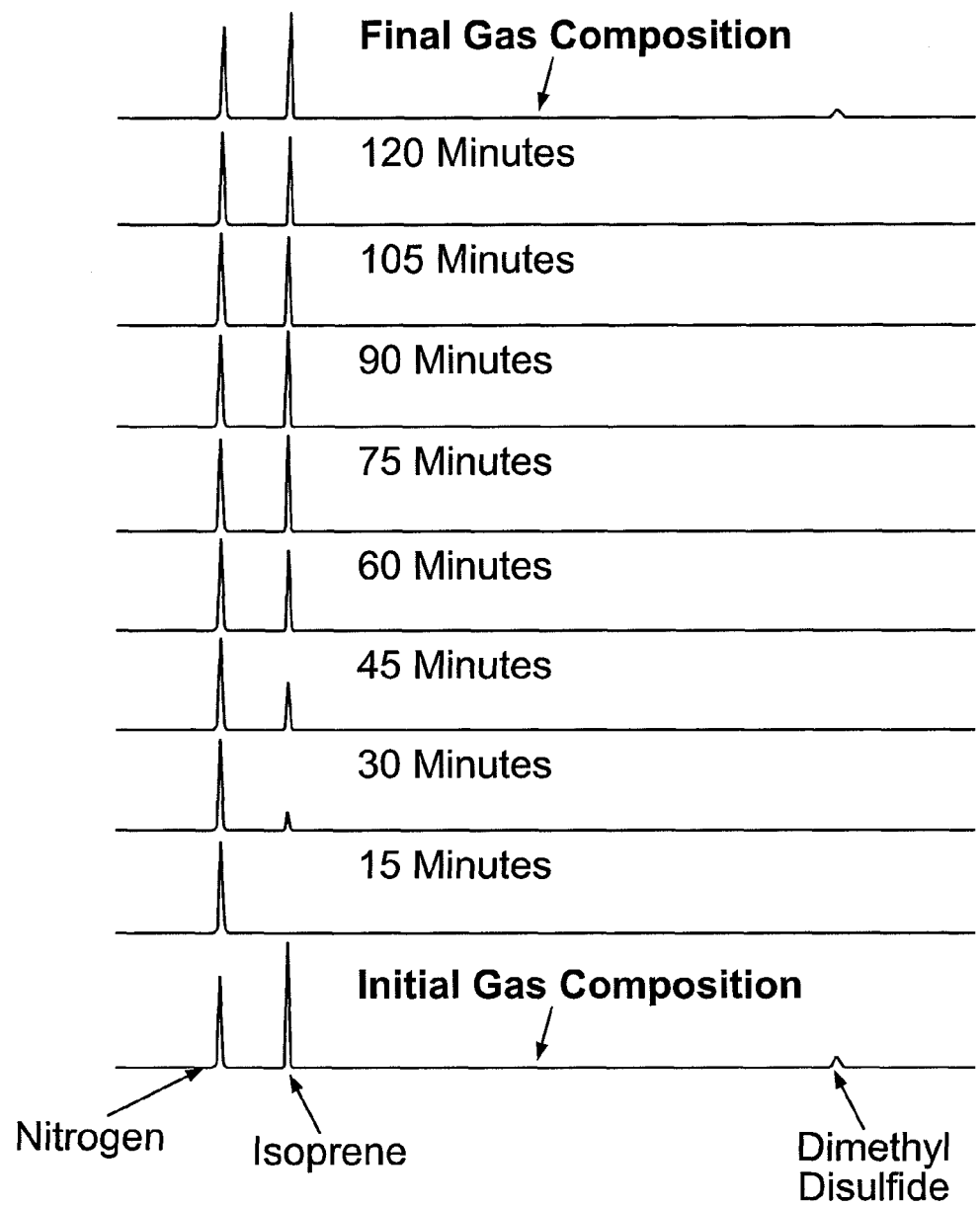
FIG. 9 is another plot of dimethyl disulfide concentration over time.

Further FIG. 9 shows, in terms of relative concentrations, the presence of nitrogen, isoprene and dimethyl disulfide in the isoprene solution at various times during the adsorption technique, showing the same effect as FIG. 8. This illustrates the initial gas composition (pre-treatment) at the lowest plot proceeding to the end of a cycle of the process at the upper plot, that the dimethyl disulfide was essentially eliminated while the amounts of the other two compounds, which are the dissolved nitrogen and the isoprene, were essentially the same. Note that at 120 minutes the dimethyl disulfide peak reappears when the saturated bed allows the dimethyl disulfide to "break through."

The above examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric pressure. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of purifying isoprene from a fermentor off-gas comprising:
    contacting a fermentor off-gas, wherein the off-gas comprises a bioisoprene composition comprising isoprene, volatile impurity, and bio-byproduct impurity, with a solvent in a first column to form:
    an isoprene-rich solution comprising the solvent, a major portion of the isoprene and a major portion of the bio-byproduct impurity present in the off-gas; and
    a vapor comprising a portion of the volatile impurity present in the off-gas;
    transferring the isoprene-rich solution from the first column to a second column; and
    stripping isoprene from the isoprene-rich solution in the second column to form:
    an isoprene-lean solution comprising a portion of the bio-byproduct impurity present in the off-gas; and
    a purified isoprene composition.

2. The method of claim 1 wherein the volatile impurity comprises a compound selected from the group consisting of $H_2O$, $CO_2$, $N_2$, $H_2$, CO and $O_2$.

3. The method of claim 1, wherein the bio-byproduct impurity comprises a compound selected from the group consisting of ethanol, acetone, methanol, acetaldehyde, methacrolein, methyl vinyl ketone, 3-methylfuran, 2-methyl-2-vinyloxirane, cis- and trans-3-methyl-1, 3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, (E)-3,7-dimethyl-1,3,6-octatriene, (Z)-3,7-dimethyl-1,3,6-octatriene, (E,E)-3,7,11-trimethyl-1,3,6,10-dodecatetraene, (E)-7,11-dimethyl-3-methylene-1,6,10-dodecatriene,3-hexen-1-ol,3-hexen-1-yl acetate, limonene, geraniol (trans-3, 7-dimethyl-2,6-octadien-1-ol), and citronellol (3,7-dimethyl-6-octen-1-ol).

4. The method of claim 1, wherein the solvent has a boiling point of greater than about 177° C.

5. The method of claim 1, wherein the solvent has a $CO_2$ Ostwald coefficient at 54° C. of less than about 1.25.

6. The method of claim 1, wherein the solvent has a Kauri-butanol value of less than about 50.

7. The method of claim 1, wherein the solvent has an Aniline Point of greater than about 66° C.

8. The method of claim 1, wherein the solvent has a kinematic viscosity at 40° C. is less than about 2.5 centistokes (cSt).

9. The method of claim 1, wherein the solvent has a surface tension at 25° C. from about 20 to 30 dyne/cm.

10. The method of claim 1, wherein the solvent has an average molecular weight from about 125 to about 225 u.

11. The method of claim 1 wherein the solvent is an iso-paraffin or a paraffin.

12. The method claim 1, wherein the solvent further comprises a polymerization inhibitor.

13. The method of claim 1, further comprising reducing the temperature of the fermentor off-gas prior to contacting the solvent in the first column.

14. The method of claim 1, further comprising transferring the fermentor off-gas to an isolation unit, thereby stabilizing the off-gas pressure, prior to contacting the fermentor off-gas with the solvent in the first column.

15. The method of claim 1, further comprising at least partially condensing the fermentor off-gas prior to contacting the solvent in the first column.

16. The method of claim 1, wherein the contacting the fermentor off-gas with a solvent in a first column comprises supplying stripping vapor from a bottom of the first column.

17. The method of claim 1, wherein the contacting the fermentor off-gas with a solvent in a first column further comprises adding steam to the first column.

18. The method of claim 1, wherein the stripping isoprene from the isoprene-rich solution in the second column comprises adding steam to the second column.

19. The method of claim 1, further comprising:
purifying the isoprene-lean solution to remove a major portion of the bio-byproduct impurity; and
transferring the isoprene-lean solution to the first column for reuse.

20. The method of claim 19, wherein purifying the isoprene-lean solution comprises treating the isoprene-lean solution with an adsorption system.

21. The method of claim 19, wherein purifying the isoprene-lean solution comprises distillation.

22. The method of claim 1, further comprising reducing the temperature of the isoprene-lean solution prior to removing a major portion of the bio-byproduct impurity.

23. The method of claim 1, comprising further purifying the purified isoprene composition.

24. The method of claim 23, wherein further purifying the purified isoprene composition comprises distillation.

25. The method of claim 23, wherein further purifying the purified isoprene composition comprises treating the purified isoprene composition with an adsorption system.

26. The method of claim 1, further comprising removing from the vapor a portion of the isoprene.

27. The method of claim 1, wherein the fermentor off-gas is provided to the first column at a pressure greater than atmospheric.

28. The method of claim 1, wherein the purified isoprene composition has a purity greater than about 90%.

29. The method of claim 1, wherein the purified isoprene composition comprises less than about 25% bio-byproduct impurity relative to the amount of bio-byproduct impurity of the fermentor off-gas.

30. The method of claim 1, wherein the purified isoprene composition comprises less than about 25% volatile impurity relative to the amount of volatile impurity of the fermentor off-gas.

31. A purified isoprene composition prepared by the method of claim 1.

32. The method of claim 23, wherein the further purifying comprises contacting the purified isoprene composition with water or a base and water.

33. A method of purifying isoprene from a fermentor off-gas comprising:
contacting a fermentor off-gas comprising isoprene, volatile impurity, and bio-byproduct impurity, with a solvent in a first column to form:
an isoprene-rich solution comprising the solvent, a major portion of the isoprene and a major portion of the bio-byproduct impurity present in the off-gas; and
a vapor comprising a portion of the volatile impurity present in the off-gas;
transferring the isoprene-rich solution from the first column to a second column; and
stripping isoprene from the isoprene-rich solution in the second column to form:
an isoprene-lean solution comprising a portion of the bio-byproduct impurity present in the off-gas; and
a purified isoprene composition; further comprising extracting at least one of methanol, acetone, or methyl acetate from the isoprene-lean solution.

* * * * *